US012125605B2

(12) United States Patent
Marsden et al.

(10) Patent No.: US 12,125,605 B2
(45) Date of Patent: Oct. 22, 2024

(54) ROTATING HOOP CHOPPER WHEEL FOR X-RAY IMAGERS

(71) Applicant: Viken Detection Corporation, Burlington, MA (US)

(72) Inventors: Lane Marsden, Reading, MA (US); Peter J. Rothschild, Newton, MA (US)

(73) Assignee: Viken Detection Corporation, Burlington, MA (US)

( * ) Notice: Subject to any disclaimer, the term of this patent is extended or adjusted under 35 U.S.C. 154(b) by 0 days.

(21) Appl. No.: 18/349,075

(22) Filed: Jul. 7, 2023

(65) Prior Publication Data
US 2024/0013947 A1    Jan. 11, 2024

Related U.S. Application Data

(60) Provisional application No. 63/367,868, filed on Jul. 7, 2022.

(51) Int. Cl.
*G21K 1/04* (2006.01)
*A61B 6/40* (2024.01)
(Continued)

(52) U.S. Cl.
CPC ............ *G21K 1/043* (2013.01); *A61B 6/4078* (2013.01); *A61B 6/4266* (2013.01); *G06T 7/0012* (2013.01); *G06T 2207/10128* (2013.01)

(58) Field of Classification Search
None
See application file for complete search history.

(56) References Cited

U.S. PATENT DOCUMENTS 4,031,401 A    6/1977   Jacob
4,242,583 A    12/1980  Annis et al.
(Continued)

FOREIGN PATENT DOCUMENTS

CN    201340400 Y    11/2009
CN    107209282      9/2017
(Continued)

OTHER PUBLICATIONS

Stein, J. A. and Swift, R. D. "Flying Spot X-Ray Imaging Systems," Materials Evaluation, vol. 30; No. 7; 137-148 (1972).
(Continued)

*Primary Examiner* — Hoon K Song
(74) *Attorney, Agent, or Firm* — Sunstein LLP

(57) ABSTRACT

An x-ray imaging apparatus includes a holdable housing; an x-ray source mounted within the housing and configured to output a fan beam of x-rays; and a hoop chopper wheel rotatably mounted within the housing and comprising an x-ray attenuating material configured to block x-rays of the fan beam. The hoop chopper wheel defines a set of beam apertures of which each aperture is configured to pass therethrough a corresponding angular portion of x-rays from the fan beam, so that rotation of the hoop chopper wheel causes scanning of the corresponding angular portion of x-rays. The x-ray source may be a transmission-type x-ray tube configured to output the fan beam centered in an x-ray extraction direction forming an angle greater than 0 degrees with respect to a longitudinal axis of the x-ray tube.

27 Claims, 23 Drawing Sheets

(51) Int. Cl.
*A61B 6/42* (2024.01)
*G06T 7/00* (2017.01)

(56) References Cited

U.S. PATENT DOCUMENTS

| | | | |
|---|---|---|---|
| 4,260,898 A | 4/1981 | Annis | |
| 4,314,146 A | 2/1982 | Berney | |
| 4,315,146 A | 2/1982 | Rudin | |
| 4,342,914 A * | 8/1982 | Bjorkholm | G01N 23/043 378/146 |
| 4,472,822 A | 9/1984 | Swift | |
| 4,503,332 A | 3/1985 | Annis | |
| 4,646,339 A | 2/1987 | Rice | |
| 4,799,247 A | 1/1989 | Annis et al. | |
| 4,809,312 A | 2/1989 | Annis | |
| 5,022,062 A | 6/1991 | Annis | |
| 5,103,099 A | 4/1992 | Bourdinaud et al. | |
| 5,179,581 A | 1/1993 | Annis | |
| 5,181,234 A | 1/1993 | Smith | |
| 5,224,144 A | 6/1993 | Annis | |
| 5,391,878 A | 2/1995 | Petroff | |
| 5,642,394 A | 6/1997 | Rothschild | |
| 5,666,393 A | 9/1997 | Annis | |
| 5,692,028 A | 11/1997 | Geus et al. | |
| 5,764,683 A | 6/1998 | Swift et al. | |
| 5,783,829 A | 6/1998 | Sealock et al. | |
| 5,903,623 A | 5/1999 | Swift et al. | |
| 6,078,052 A | 6/2000 | DiFilippo | |
| 6,192,104 B1 | 2/2001 | Adams et al. | |
| 6,252,929 B1 | 6/2001 | Swift et al. | |
| 6,272,206 B1 | 8/2001 | Bjorkholm | |
| 6,292,533 B1 | 9/2001 | Swift et al. | |
| 6,434,219 B1 | 8/2002 | Rothschild et al. | |
| 6,451,040 B1 | 9/2002 | Purcell et al. | |
| 6,461,040 B1 | 10/2002 | Mattson et al. | |
| 6,525,320 B1 | 2/2003 | Juni | |
| 7,099,434 B2 | 8/2006 | Adams et al. | |
| 7,115,875 B1 | 10/2006 | Worstell | |
| 7,200,201 B2 | 4/2007 | Unger et al. | |
| 7,218,704 B1 | 5/2007 | Adams et al. | |
| 7,286,636 B2 | 10/2007 | Unger et al. | |
| 7,310,407 B2 | 12/2007 | Juni | |
| 7,551,715 B2 | 6/2009 | Rothschild et al. | |
| 7,593,510 B2 | 9/2009 | Rothschild | |
| 7,995,707 B2 | 8/2011 | Rothschild et al. | |
| 8,116,575 B1 | 2/2012 | Saisan et al. | |
| 8,199,996 B2 | 6/2012 | Hughes | |
| 8,774,362 B2 | 7/2014 | Hughes | |
| 8,861,684 B2 | 10/2014 | Al-Kofahi et al. | |
| 9,146,201 B2 | 9/2015 | Schubert et al. | |
| 9,285,488 B2 | 3/2016 | Arodzero et al. | |
| 10,739,491 B2 | 8/2020 | Yang et al. | |
| 10,762,998 B2 | 9/2020 | Rothschild | |
| 10,762,999 B2 | 9/2020 | Kaszuba et al. | |
| 10,770,195 B2 | 9/2020 | Rothschild | |
| 10,794,843 B2 | 10/2020 | Rothschild et al. | |
| 10,959,689 B2 | 3/2021 | Nariyuki et al. | |
| 11,200,998 B2 | 12/2021 | Rothschild | |
| 2001/0016028 A1* | 8/2001 | Adams | G01N 23/203 378/57 |
| 2004/0017888 A1 | 1/2004 | Seppi et al. | |
| 2006/0083354 A1 | 4/2006 | Tybinkowski et al. | |
| 2006/0104415 A1 | 5/2006 | Unger et al. | |
| 2006/0251214 A1 | 11/2006 | Unger et al. | |
| 2008/0037707 A1 | 2/2008 | Rothschild et al. | |
| 2008/0170661 A1 | 7/2008 | Unger et al. | |
| 2009/0086906 A1 | 4/2009 | Clayton | |
| 2009/0086907 A1 | 4/2009 | Smith | |
| 2009/0103686 A1 | 4/2009 | Rothschild | |
| 2009/0175412 A1 | 7/2009 | Grodzins et al. | |
| 2011/0058644 A1 | 3/2011 | Thran et al. | |
| 2011/0103548 A1 | 5/2011 | Bendahan | |
| 2012/0236990 A1 | 9/2012 | Rothschild | |
| 2013/0134930 A1 | 5/2013 | Konkle et al. | |
| 2013/0195248 A1 | 8/2013 | Rothschild et al. | |
| 2013/0202089 A1 | 8/2013 | Schubert et al. | |
| 2013/0208857 A1 | 8/2013 | Arodzero et al. | |
| 2013/0315368 A1 | 11/2013 | Turner | |
| 2016/0070006 A1 | 3/2016 | Konkle et al. | |
| 2017/0052125 A1 | 2/2017 | Georgeson et al. | |
| 2017/0332986 A1 | 11/2017 | Grondin et al. | |
| 2017/0358380 A1 | 12/2017 | Rothschild | |
| 2018/0294066 A1 | 10/2018 | Rothschild | |
| 2019/0043633 A2 | 2/2019 | Rothschild | |
| 2019/0242834 A1 | 8/2019 | Rothschild et al. | |
| 2019/0346382 A1 | 11/2019 | Rothschild | |
| 2019/0380664 A1 | 12/2019 | Nariyuki et al. | |
| 2020/0025968 A1 | 1/2020 | Yang et al. | |
| 2020/0326291 A1 | 10/2020 | Rothschild | |
| 2021/0005340 A1 | 1/2021 | Rothschild | |
| 2021/0074445 A1 | 3/2021 | Rothschild | |
| 2022/0003693 A1 | 1/2022 | Rothschild | |
| 2022/0091054 A1 | 3/2022 | Rothschild et al. | |

FOREIGN PATENT DOCUMENTS

| | | | |
|---|---|---|---|
| CN | 108318512 A | | 7/2018 |
| CN | 115112694 A | | 9/2022 |
| EP | 2667184 A1 | | 11/2013 |
| EP | 3399303 A1 | | 11/2018 |
| EP | 3505975 A1 | | 7/2019 |
| EP | 3399303 | * | 9/2022 |
| GB | 2084829 | | 4/1982 |
| WO | 2001/37287 A1 | | 5/2001 |
| WO | 2005079437 A2 | | 9/2005 |
| WO | 2011053972 A2 | | 5/2011 |
| WO | 2012058207 A2 | | 5/2012 |
| WO | 2012174265 A1 | | 12/2012 |
| WO | 2104058495 A2 | | 4/2014 |
| WO | 2016081881 A1 | | 5/2016 |
| WO | 2019152900 A1 | | 8/2019 |
| WO | 2019217596 A1 | | 11/2019 |

OTHER PUBLICATIONS

Case, G. L., et al., Wavelength-Shifting Fiber Readout of LaCl and LaBr scintillators, Proc. of SPIE, UV, X-Ray, and gamma-Ray Space Instrumentation for Astronomy XIV, 58980K; vol. 5898, 8 pages (2005).

Hutchinson, D. P., et al., "Optical readout for Imaging Neutron Scintillation Detectors," Proc. of SPIE; vol. 4785; 262-267 (2002).

Keizer, F., The Optimal Cosmic Ray Detector for High-Schools, HiSparc Collaboration, 2011.

Maekawa, T., et al., "Thin Beta-ray Detectors using Plastic Scintillator Combined with Wavelength-shifting Fibers for Surface Contamination Monitoring," Journal of Nuclear Science and Technology, vol. 35; No. 12; pp. 886-894 (1998).

Nishikido, F., et al., "X-ray Detector made of Plastic Scintillators and WLS fiber for real-time dose Distribution Monitoring in Interventional Radiology," IEEE Nuclear Science Symposium and Medical Imaging Conference (NSS/MIC), pp. 1272-1274 (2012).

Worstell, W., et al., "Scintillator Crystal Readout with Wavelength-Shifting Optical Fibers," IEEE, pp. 1869-1873 (1995).

Van Liew, S., "New Developments in Portable Backscatter Systems"; Civil Action No. 1:19-cv-10614-NMG, filed Apr. 29, 2019 (43 pages).

Mini Z Handheld Z Backscatter Screening System Overview, Civil Action No. 1:19-cv-10614-NMG, filed Apr. 29, 2019 (18 pages).

European Patent Office; Invitation to pay addiditonal fees, International Search Report and Written Opinion prepare in PCT application No. PCT/US2023/069825, dated Nov. 11, 2023 (14 pages).

European Patent Office, International Search Report issued in PCT application No. PCT/US2023/069825, dated Jan. 9, 2024, 19 pages.

* cited by examiner

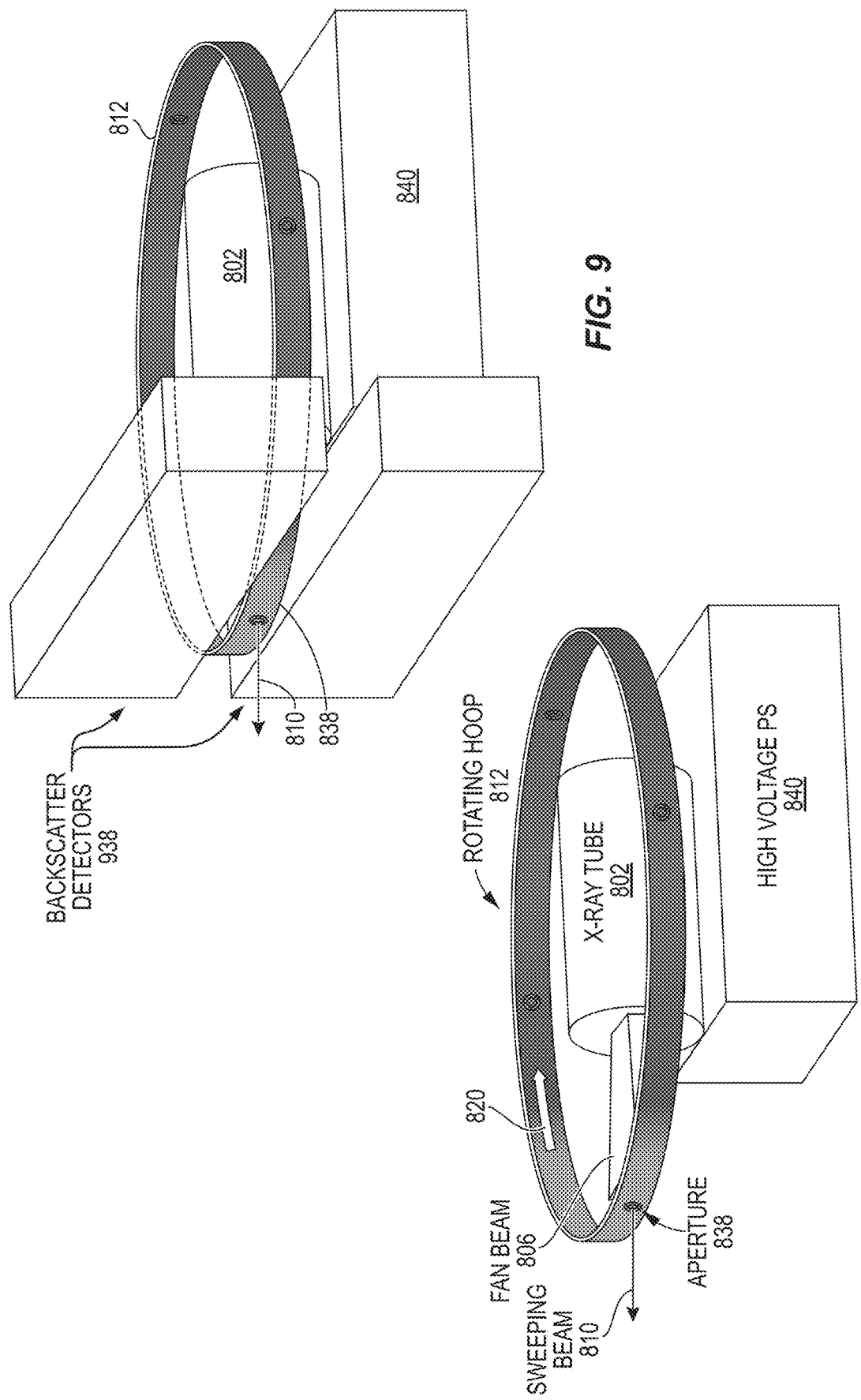

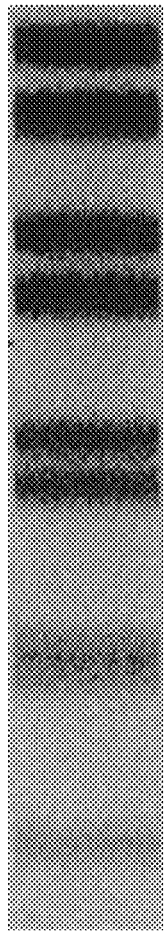  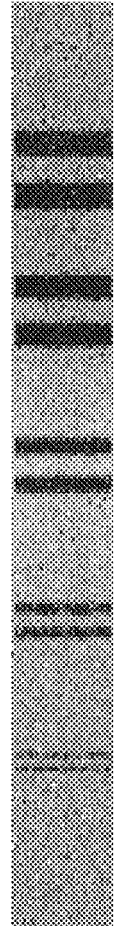
FIG. 10

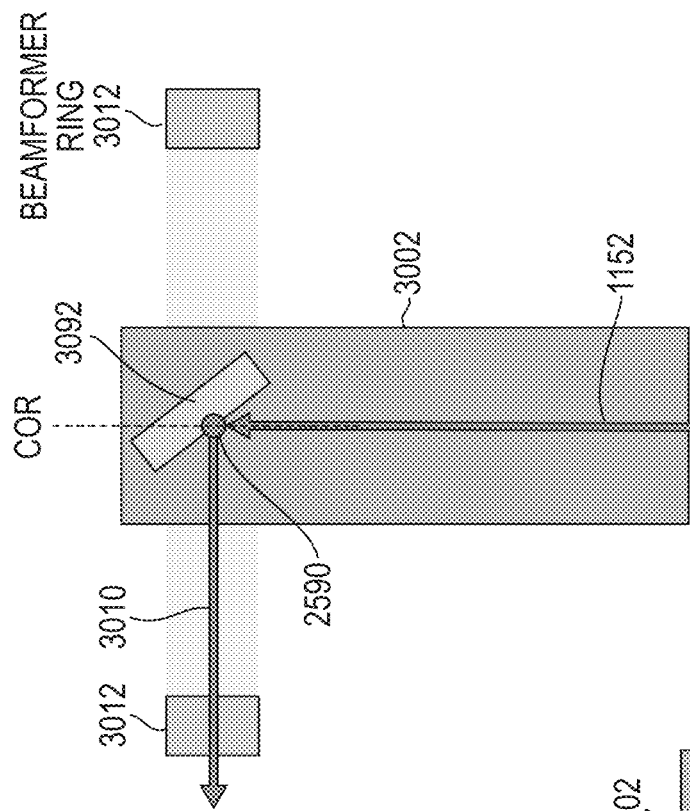
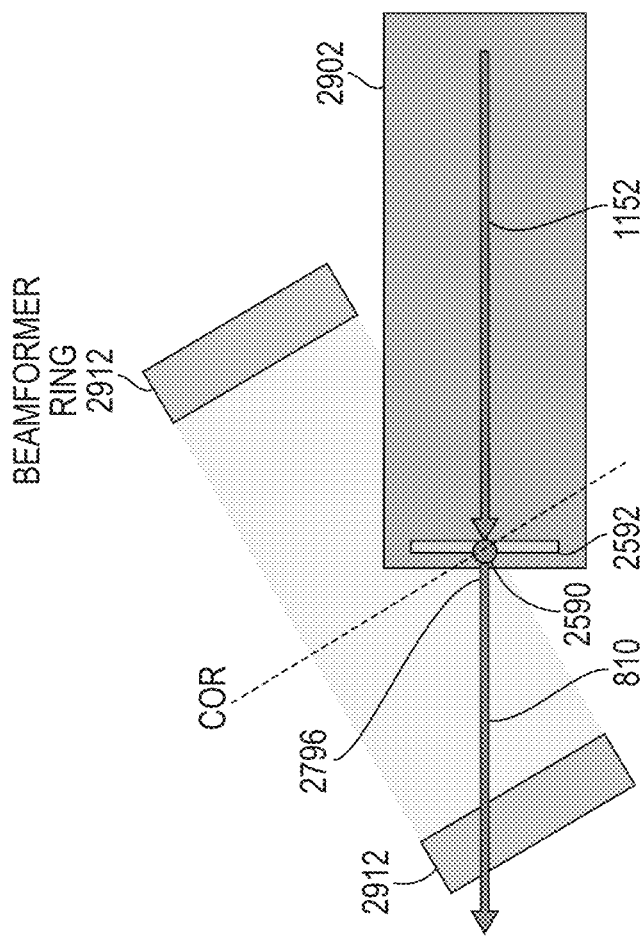

ROTATING HOOP CHOPPER WHEEL FOR X-RAY IMAGERS

RELATED APPLICATIONS

This application claims the benefit of U.S. Provisional Patent Application Ser. No. 63/367,868, filed on Jul. 7, 2022.

TECHNICAL FIELD

The present invention relates to apparatuses and methods for x-ray scanning, and particularly configurations of x-ray scanners that include hoop chopper wheels, transmission-type x-ray tubes, and a combination thereof, as well as particular transmission-type x-ray tube configurations.

BACKGROUND ART

X-ray backscatter imaging has been used for detecting concealed contraband, such as drugs, explosives, and weapons, since the late 1980's. Unlike traditional transmission x-ray imaging that creates images by detecting the x-rays penetrating through an object, backscatter imaging uses reflected or scattered x-rays to create the image. Typically, an x-ray fan beam is "chopped" into a pencil beam by a rotating "chopper wheel" containing slits or other openings. The chopper wheel is usually one of three basic types: a rotating disk, a rotating wheel, or a rotating hoop.

Handheld backscatter x-ray imagers have been available since 2014 and have used rotating disk chopper wheels.

SUMMARY OF THE EMBODIMENTS

In accordance with one embodiment, an x-ray imaging apparatus includes a holdable housing; an x-ray source mounted within the housing and configured to output a fan beam of x-rays; and a hoop chopper wheel rotatably mounted within the housing and comprising an x-ray attenuating material configured to block x-rays of the fan beam. The hoop chopper wheel defines a set of beam apertures of which each aperture is configured to pass therethrough a corresponding angular portion of x-rays from the fan beam, so that rotation of the hoop chopper wheel causes scanning of the corresponding angular portion of x-rays. The apparatus may optionally include features of second and third embodiments summarized in following, as well as other embodiments described herein.

Consistent with a second embodiment, an x-ray imaging apparatus includes a housing; a transmission-type x-ray tube mounted within the housing and a hoop chopper wheel configured to output a fan beam of x-rays, through an exit window of the transmission-type x-ray tube, centered in an x-ray extraction direction forming an angle greater than 0 degrees with respect to an longitudinal axis of the transmission-type x-ray tube; and a hoop chopper wheel rotatably mounted within the housing and including an x-ray attenuating material configured to block x-rays of the fan beam, the hoop chopper wheel defining a set of beam apertures of which each aperture is configured to pass therethrough a corresponding angular portion of x-rays from the fan beam, so that rotation of the hoop chopper wheel causes scanning of the corresponding angular portion of x-rays. The second embodiment may optionally including any features summarized in connection with the first and third embodiments and other embodiments described herein.

Consistent with a third embodiment, an x-ray tube includes a transmission anode configured to receive electrons accelerated in a longitudinal axis of the x-ray tube and to produce source x-rays thereby; and an x-ray collimator configured to collimate the source x-rays for output as a fan beam of x-rays centered in an x-ray extraction direction forming an angle greater than 0 degrees with respect to the longitudinal axis of the transmission-type x-ray tube.

BRIEF DESCRIPTION OF THE DRAWINGS

The features of embodiments will be more readily understood by reference to the following detailed description, taken with reference to the accompanying drawings, in which:

FIG. 8 is a perspective-view diagram illustrating a scanning module with an in-line hoop chopper wheel that may be used in the present x-ray imaging apparatus embodiments.

FIG. 9 is a perspective-view diagram illustrating a scanning module that may be used in present embodiments, along with an example placement of backscatter detectors relative to a hoop chopper wheel.

FIG. 10 shows computer-simulated backscatter images of a line-pair phantom acquired with a prior-art Viken Detection™ HBI™ handheld x-ray scanner with a disk chopper wheel (upper image) compared to images acquired with embodiment hoop-type chopper assemblies with 1.0 mm square and 0.5 mm×10 mm rectangular apertures (middle and lower images, respectively).

FIGS. 25-30 are cross-sectional view diagrams of various example x-ray tube oriented relative to hoop chopper wheels as part of embodiments.

FIG. 25 shows a tilted transmission x-ray tube with in-line hoop with a clearance notch.

FIG. 26 is similar to FIG. 25 but illustrates design consequences of omitting the clearance notch.

FIG. 27 shows a straight transmission x-ray tube functioning with an offset hoop chopper wheel.

FIG. 28 shows a straight transmission x-ray tube functioning with an inline hoop chopper wheel.

FIG. 29 shows a straight transmission x-ray tube functioning with a tilted, in-line hoop chopper wheel.

FIG. 30 illustrates a reflection-type anode x-ray tube functioning with an in-line hoop chopper wheel in an embodiment.

Figure 1:
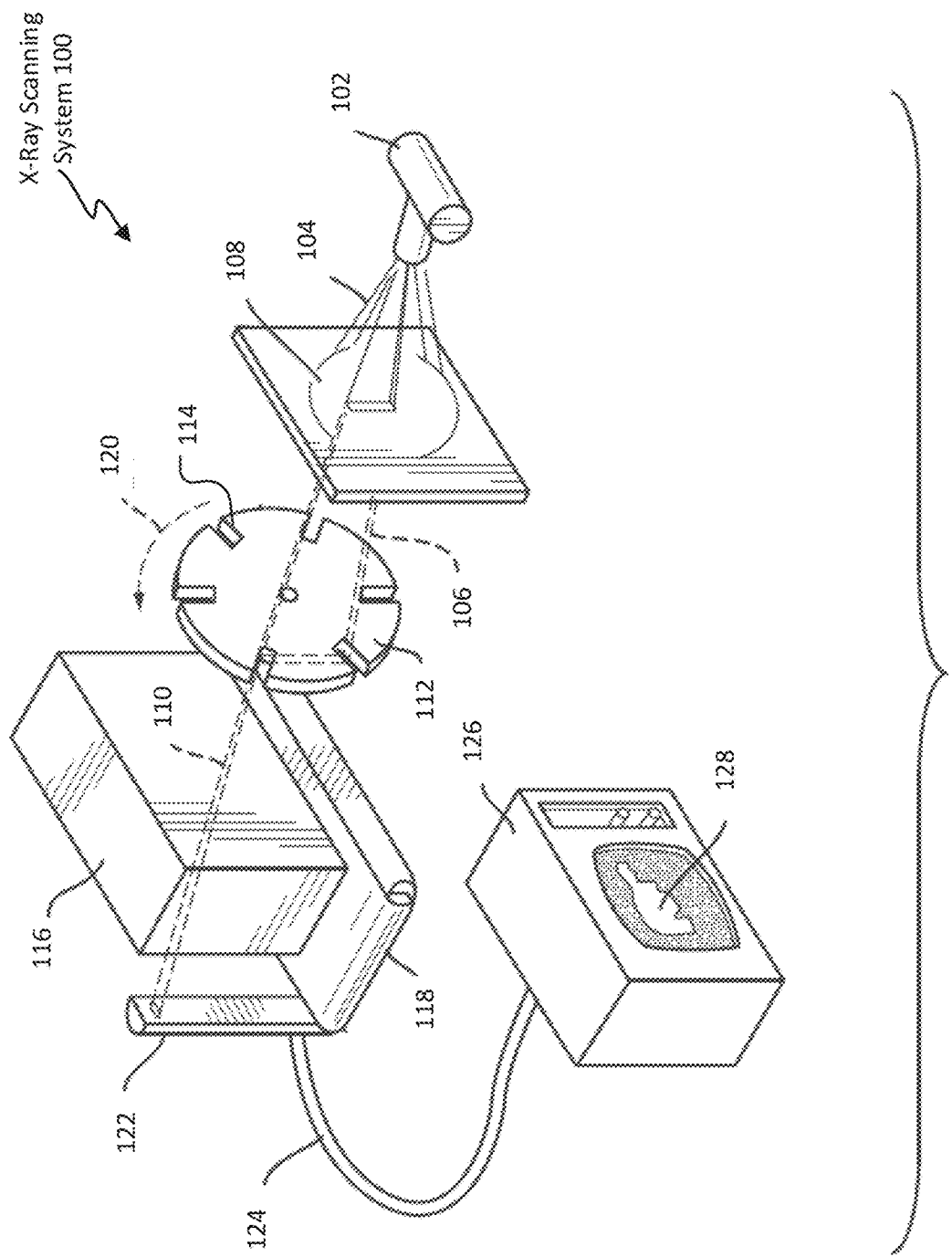
FIG. 1 (prior art) is a perspective-view illustration of an x-ray transmission imaging system utilizing a scanning beam of x-rays, the illustration showing principles applicable to backscatter and transmission x-ray imaging implemented in embodiment systems.

The foregoing will be apparent from the following more particular description of example embodiments, as illustrated in the accompanying drawings in which like reference characters refer to the same parts throughout the different views. The drawings are not necessarily to scale, emphasis instead being placed upon illustrating embodiments.

DETAILED DESCRIPTION OF SPECIFIC EMBODIMENTS

Definitions

As used in this description and the accompanying claims, the following terms shall have the meanings indicated, unless the context otherwise requires:

A "set" includes at least one member.

"Target object," "target," and "object" are used interchangeably herein and refer to a subject that may be scanned by an x-ray scanner for imaging.

"Holdable" means capable of being held and of a size and character that makes holding during scanning use possible by a human, a robot, or a drone. "Holdable" includes "mountable" when a human, robot, or drone to do the "holding." "Holdable may be selected from the group consisting of hand holdable, arm holdable, robotically holdable, robotically mountable, articulated-arm-holdable, drone holdable, and combinations thereof

Certain Existing Instruments

Handheld backscatter x-ray imagers have been available beginning with a 70 kV version in 2014. The first higher-energy 120 kV model capable of imaging objects through steel was developed by Heuresis Corporation (now Viken Detection™ Corporation) and was first available in 2016. A higher-energy version operating at 140 kV called the Nighthawk™ became available a few years later. Another 140 kV imager became available in 2019. All these systems use a rotating tungsten disk with four slits, and the disk is irradiated at a normal angle by an incident fan beam from the x-ray source.

The existing Viken Detection™ handheld backscatter x-ray instruments all use an open-geometry rotating disk chopper wheel with scatter plates as described in US Pat. Nos. 10,770,195 and 11,200,998.

A disadvantage of using a chopper disk in a handheld instrument is that the disk and associated shielding and collimators can take up quite a lot of space and add substantial weight, which may be borne by an operator, often for extended periods of time. As an example, the chopper disk and associated pre-collimator and post-collimator shielding in the Viken Detection™ HBI-120™ system weighs about 1.2 lbs.

Another disadvantage of using a disk chopper wheel is that due to its potential size and highly attenuating materials, the disk is typically installed behind the backscatter detector assembly. This typically requires the disk to be installed at least one inch (and usually much more) behind a front face of the instrument. Due to the divergence of the pencil beam as it exits the chopper disk assembly, the scanning pencil beam may be substantially wider than the slit apertures in the disk at a position where the beam exits the front face of the instrument. Since the imaging resolution of the instrument is determined by the width of the beam at the point it irradiates the target object, the image resolution may be degraded compared to what could be achieved if the disk were located right at the front face of the instrument, and not located behind the backscatter detectors.

General Features of Embodiments

Accordingly, it would be desirable to have a chopper wheel assembly that could both reduce weight and provide higher resolution, especially for a handheld x-ray imaging device.

This application discloses a novel hoop chopper assembly that can be used instead of a disk in a handheld backscatter x-ray imaging instrument. An inner surface of a narrow rotating hoop of x-ray attenuating material such as tungsten can be irradiated by a fan beam emitted from an x-ray source. Apertures in the hoop can allow some of the x-rays in the fan beam to pass through, creating a pencil beam of x-rays that sweeps from side to side as the hoop rotates about the source. The apertures can be circular, ellipsoidal, or rectangular slits. The hoop can be made narrow enough so that the irradiated apertures within the hoop can be located very close to the front of the instrument without interfering with the backscatter detector assembly. This means that the beam width at a position where the beam exits the front of the instrument can be almost identical to the aperture width, resulting in much higher resolution than can be achieved with the disk chopper assembly set back into the instrument.

Further Examples in the Prior Art

FIG. 1 (prior art) illustrates basic principles of backscatter imaging in reference to a transmission imaging system 100 that uses a scanning x-ray beam in a manner similar to a backscatter imaging system. A standard x-ray tube 102 generates source x-rays 104 that are collimated into a fan beam 106 by a slit aperture in attenuating plate 108. The fan beam 106 is then "chopped" into a scanning pencil beam 110 by a rotating "chopper wheel" 12 defining slit apertures (which may also be referred to herein as "slits") 114 therein. The scanning pencil beam 110 thus scans over target object 116 (in this example a suitcase on a conveyor 118 being imaged as the chopper wheel 112 rotates with a rotation 120.

In the transmission imaging system 100 as illustrated, x-rays of the scanning pencil beam 110 that are transmitted through the target 116 are detected by a transmission x-ray detector 122, which outputs a signal via a signal cable 124 to a monitor 126, which shows an image 128 of contents of the target 116. In the same type of system, while not shown in FIG. 1, backscatter x-ray detectors may be positioned to detect x-rays from the pencil beam 110 that are scattered by the target 116 in a general or specific backward direction, such as in a vicinity between the target 116 and the chopper wheel 112. An intensity of the x-rays scattered in the backwards direction may be thus recorded by one or more large-area backscatter detectors (not shown) as a function of the position of the irradiating beam. In the case of backscatter detectors, it can be advantageous to use large-area detectors in order to detect the greatest number of x-rays scattered in various specific backward directions. By moving the object through the plane containing the scanning beam, either on a conveyor 118 or under its own power, a two-dimensional backscatter image of the object may be obtained.

Figure 2:
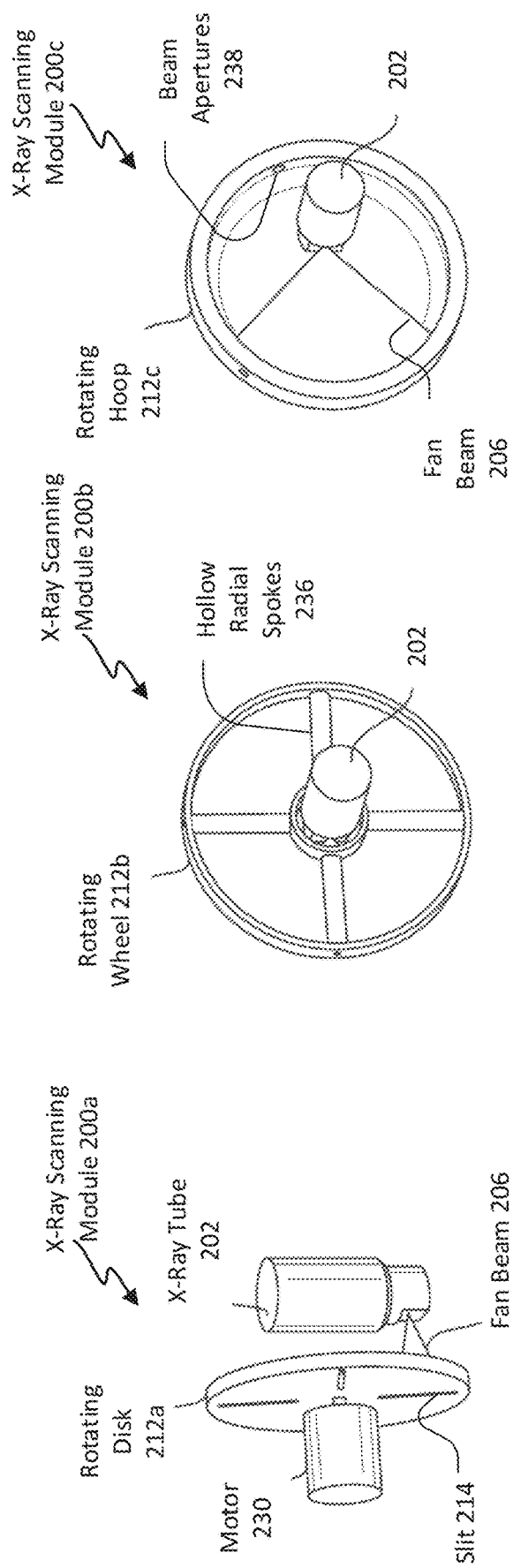
FIGS. 2A-2C (prior art) illustrate rotating disk, rotating wheel, and rotating hoop types of x-ray chopper wheels, respectively, that have been used for backscatter imaging systems.

FIGS. 2A-2C (prior art) illustrate three different types of existing x-ray chopper wheels used for generating a scanning pencil beam from a substantially stationary wide x-ray beam emanating either directly from an x-ray tube 202 or from the x-ray tube 202 and through an intermediary collimation plate such as the collimation plate 108 of FIG. 1, for example. The chopper wheel of existing x-ray backscatter imaging systems usually is one of three basic types: a rotating disk chopper wheel (which may also referred to herein as a "disk" or "disk chopper wheel") 212a, a rotating wheel chopper wheel (which may also be referred to herein as a "hub-and-spoke" chopper wheel) 212b, or a rotating hoop chopper wheel (which may also be referred to herein as a "hoop" chopper wheel) 212c. The three types are shown in FIGS. 2A, 2B, 2C, respectively, in x-ray scanning modules 200a, 200b, 200c, respectively. The chopper wheels 212a, 212b, 212c can be rotatably mounted in various ways that are known in the art of x-ray scanning. FIG. 2A illustrates one way of causing a chopper wheel to rotate, wherein the disk chopper wheel 212a is coupled to a shaft of a motor 230. Slits 214 defined within the disk chopper wheel 212a serve a purpose similar to that of the slits 114 in FIG. 1. A fan beam 206 from the x-ray tube 202 irradiates the rotating disk 212a. The rotating wheel 212b of FIG. 2B includes hollow radial spokes 236 that allow x-rays to pass therethrough to create a scanning pencil beam. The rotating hoop chopper wheel 212c of FIG. 2C includes apertures 238 defined in the hoop to allow x-rays from the fan beam 206 to pass therethrough to output the scanning pencil beam as the hoop chopper wheel 212c rotates.

Various benefits and disadvantages of each type of chopper wheel are summarized below.

Rotating Disk

Figure 3:
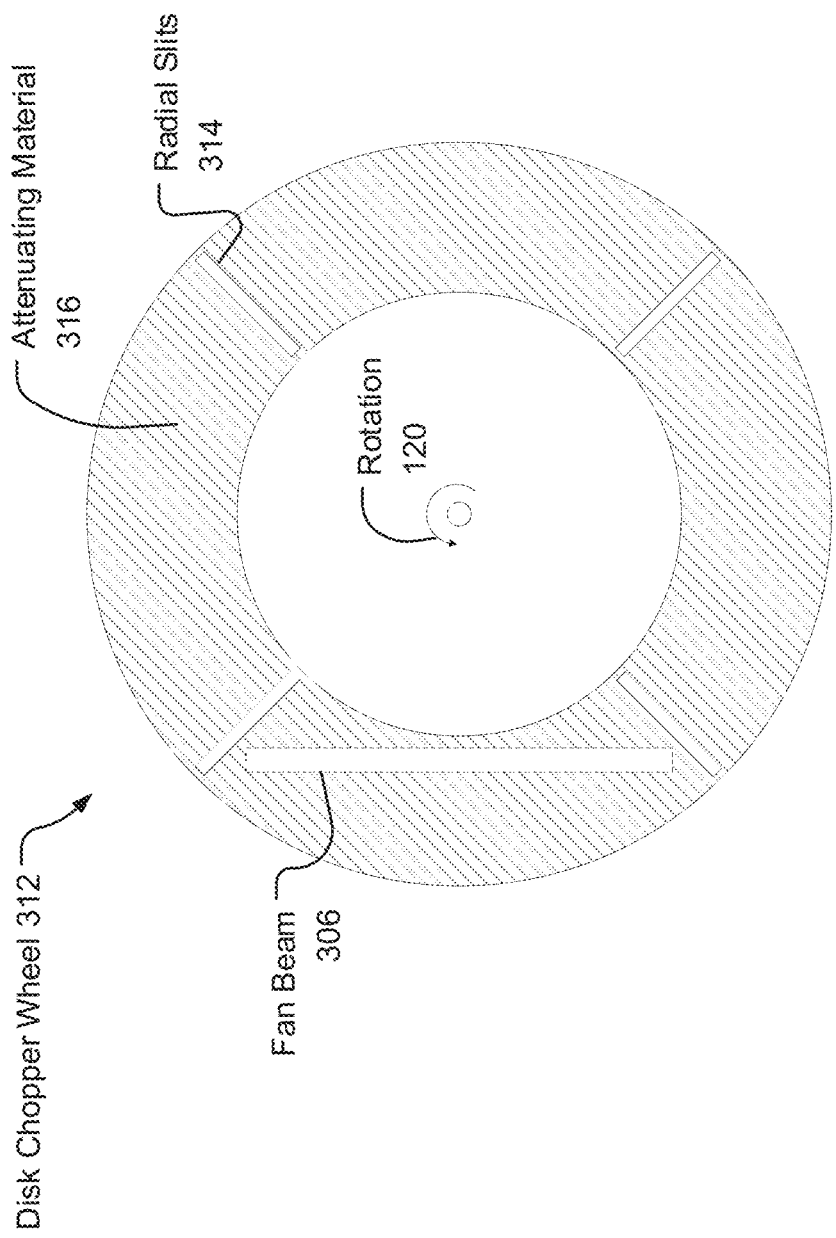
FIG. 3 (prior art) is a plan-view diagram of a rotating disk chopper wheel, showing its radial slits and a region irradiated by a fan beam of x-rays.

FIG. 3 illustrates a rotating disk, or disk chopper wheel 312, which is typical of designs used in the earliest x-ray imaging systems. Initially, the rotating disk was used to create a digital transmission x-ray imaging system, such as the system 100 illustrated in FIG. 1. Then backscatter imaging was added by incorporating additional backscatter detectors into the system. The disk chopper wheel 312 design includes a disk of attenuating material 316, such as lead or tungsten, with a series or radial slits 314 defined therein, which allow x-rays to pass through. The disk chopper wheel 312 is irradiated with a fan beam of x-rays 306. The intersection of the fan beam 306 with a radial slit 314 allows a "pencil beam" of x-rays, such as the pencil beam 110 in FIG. 1, to pass through. As the disk rotates with the rotation 120, the pencil beam of x-rays scans within a plane of the incident fan beam, with the scan direction defined by a line of sight from a focal spot of an x-ray tube (not illustrated in FIG. 3) through the irradiated slit 314. If the fan beam is vertical, then the pencil beam scans up and down. Alternatively, if the fan beam is oriented horizontally, then the pencil beam scans from side to side as the disk chopper wheel rotates. A chopper wheel of this design has been used in baggage scanning systems, which can operate at an x-ray endpoint energy of between 120 kV and 180 kV. The first two systems used an aluminum wheel with a ring of lead providing the attenuating material in the region where the disk intersects the irradiating fan beam. Four radial slits in the lead with slit edges defined by tungsten "jaws" create four sweeping pencil beams per full rotation of the disk chopper wheel. Alternatively, a solid tungsten disk with slits machined into it can be used.

A disk chopper wheel can be normally irradiated, as shown in FIG. 2A, in which a center of the fan beam 206 irradiates the rotating disk 212a at a substantially perpendicular angle with respect to a surface of the rotating disk 212a.

Figure 4:
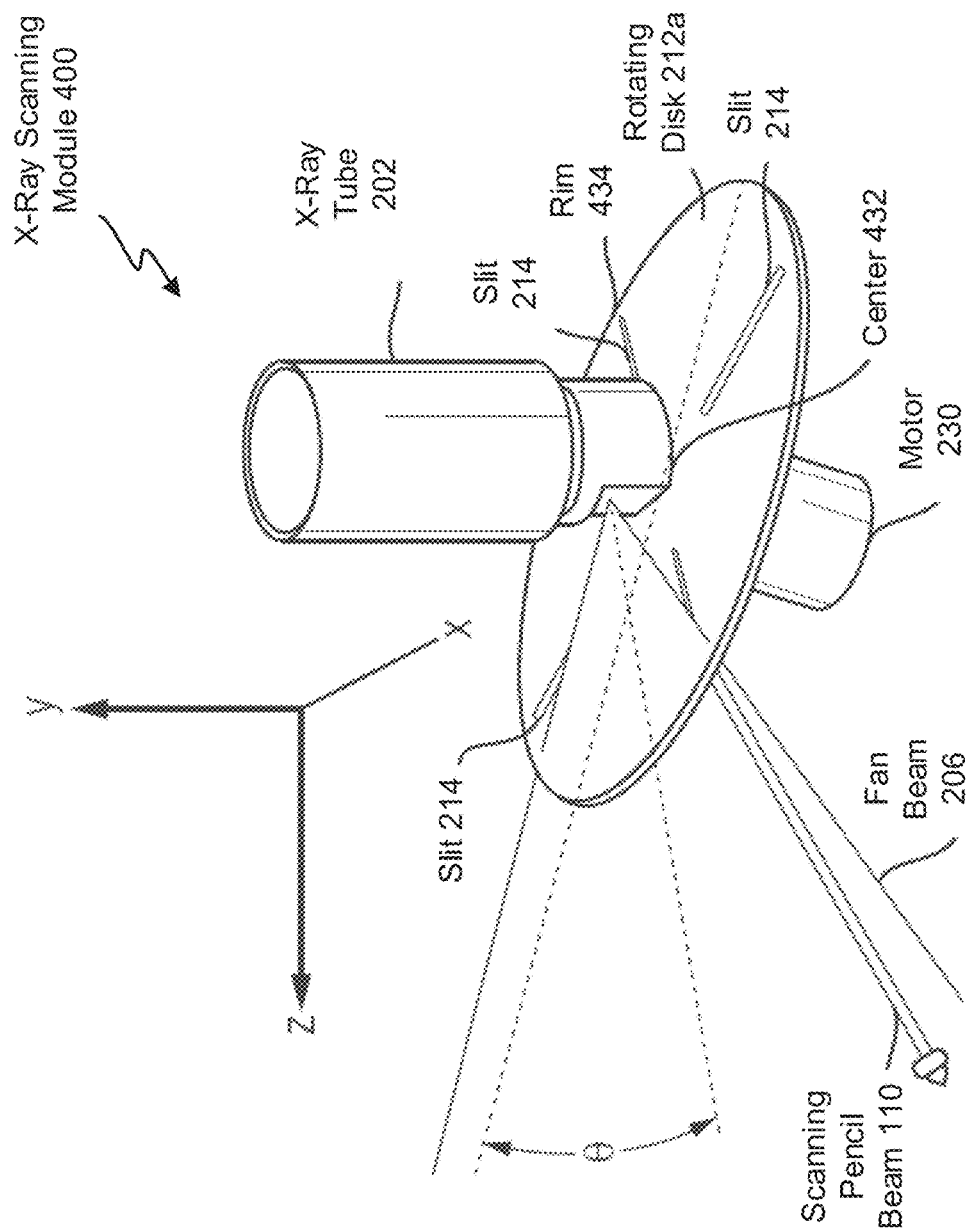
FIG. 4 (prior art) is a perspective-view illustration of an x-ray scanning module in which an irradiating fan beam of x-ray radiation is incident on a surface of a tilted or "angled" disk chopper wheel at an angle substantially different from the normal.

FIG. 4 (prior art) illustrates an alternative x-ray scanning module 400. The module 400 is a more recent modification of the x-ray scanning module 200a of FIG. 2A, which has been modified in the x-ray scanning module 400 in a "tilted chopper wheel" (also referred to as an "angled chopper wheel") configuration to significant advantage. The x-ray scanning module 400 can be a particularly compact and relatively low-weight x-ray scanning module. This design is particularly advantageous in mobile scanning device applications, as it allows a smaller and lower-cost motorized vehicle with a lower maximum chassis load limit to be used. In a larger, vehicle- or cart-based mobile scanning system, it also allows a vehicle, trailer, or cart that supports the x-ray scanning module to be smaller, lighter, and more maneuverable. Thus, where the embodiments described herein may not have even been feasible or desirable previously, given the weight, expense, and difficulty of handling two massive chopper wheels in a given system, or one such massive chopper wheel on a mobile conveyance, the tilted design can solve the long-standing associated problems. Tilted disk chopper wheels are described more fully in U.S. Pat. No. 10,762,998, which is hereby incorporated by reference herein in its entirety. This chopper wheel assembly is compact, and by tilting the disk, the assembly enables a disk chopper wheel design to be used more easily at x-ray energies above 200 kV. The compactness and low weight of the tilted disk chopper wheel x-ray scanning module makes it ideal to be used on a mobile platform, and especially for a mobile dual-sided inspection system for embodiment x-ray scanning modules, systems, and methods described herein.

FIG. 4 particularly illustrates an orientation of a fan beam 406 output from the x-ray tube 202 and the disk chopper wheel 212a in greater detail. The x-ray tube 202 is oriented with an axis in the Y direction. The fan beam 206 of source x-rays that are output from the x-ray tube 202 is oriented in the X-Z plane (the X-Z plane contains the fan beam 206). The plane of rotation of the chopper disk lies at an oblique non-perpendicular angle Θ to the X-Z plane. The scanning pencil beam 110 also is scanned in the X-Z plane, i.e., the beam plane, as the chopper disk rotates. The disk chopper wheel 212a includes a rim 434 and center 432, and the slits 214 are oriented to extend radially toward the rim and center. The rotating disk chopper wheel 212a is rotated by means of the motor 230.

The chopper disk 212a is not oriented in either the X-Z plane or the X-Y plane, but, rather, in a disk plane that is at an angle Θ with respect to the beam plane (X-Z plane) of the fan beam 206. The disk plane can also be referred to as a plane of rotation (or rotational plane) of the chopper disk 212a, because the disk remains parallel to this plane as it rotates. The disk plane can be parallel to the X axis. By positioning the plane of the rotating disk at an acute (substantially non-perpendicular) angle Θ to the plane of the fan beam, the actual thickness of the disk can be reduced by a factor $F=1/\sin(\Theta)$ while keeping the disk's effective thickness the same. As used herein, "substantially non-perpendicular" indicates that the angle Θ is small enough to increase effective thickness significantly, such as increasing effective thickness by more than 25%, more than 50%, more than 100% (an effective thickness multiplier of 2), more than 200%, or more than 400%.

The rotating disk is the only chopper wheel type that has been used in handheld backscatter x-ray imaging systems prior to this application. Available 140 kV systems all use a normally irradiated, rotating tungsten disk defining four slits.

Rotating Wheel

The second type of the "chopper wheel" was developed for use in a mobile backscatter imaging platform that operates at an x-ray endpoint energy of 450 kV. At these energies, a rotating disk of the standard normally irradiated design would have to be much too thick to provide enough attenuation for the incident x-rays. Thus, that solution included designing a large wheel with the x-ray tube located at its center. Hollow radial "spokes" 236, as illustrated in FIG. 2B, allow the x-rays to escape. As the wheel rotates about the stationary x-ray tube 202, scanning pencil beams of x-rays are emitted, which can scan a target object to be imaged. Enough shielding can then be incorporated into the hub of the wheel to provide the required attenuation. The problem with the rotating wheel or "hub and spoke" design was its sheer size and weight (the wheel had a diameter of several feet), and its maximum rotation speed is a few hundred rotations per minute. Because the x-ray tube is located inside the hub of the wheel, a bipolar x-ray tube can be used. However, the bearings supporting the wheel must have a diameter larger than that of the x-ray tube, and large bearings are inherently expensive and typically have a much lower maximum rotation speed.

Rotating Hoop

A third type of chopper wheel that has been used in backscatter imaging systems is the rotating hoop, as exemplified by the rotating hoop 212c of FIG. 2C. These were first used for a baggage scanner designed for enhanced detection. This mobile scanner system operates at only 225 kV, which is half the endpoint energy of the earlier 450 kV system. Unlike the 450 kV x-ray tube, the 225 kV tube has a unipolar design, which allows it to be used inside a rotating hoop chopper wheel. The hoop chopper wheel design includes a rotating hoop of aluminum or steel, with a band of highly attenuating material (such as lead) located in the outer rim. A fan beam of radiation emitted from the x-ray tube located inside the hoop is incident on the inner surface of the hoop rim. The apertures 238 in the attenuating material in the rim allow the x-rays to pass through, creating a beam of x-rays that sweeps across the object being imaged as the hoop rotates. The advantage of this design over the wheel is that it can have smaller bearings and can typically spin faster. In existing hoop designs, all the shielding is in the rim, typically yielding a high moment of inertia and creating large stresses in the hoop material.

Handheld X-Ray Imagers

Handheld backscatter x-ray imagers have been available beginning with a 70 kV version. The first higher-energy 120 kV model capable of imaging objects through steel (the HBI-120) was developed by Heuresis Corporation (now Viken Detection™ Corporation). A higher energy version operating at 140 kV called the Nighthawk™ was available a few years later. A 140 kV model was available later. All these systems use a rotating tungsten disk with four slits, which is normally irradiated by an incident fan beam from the x-ray source.

Figure 5:
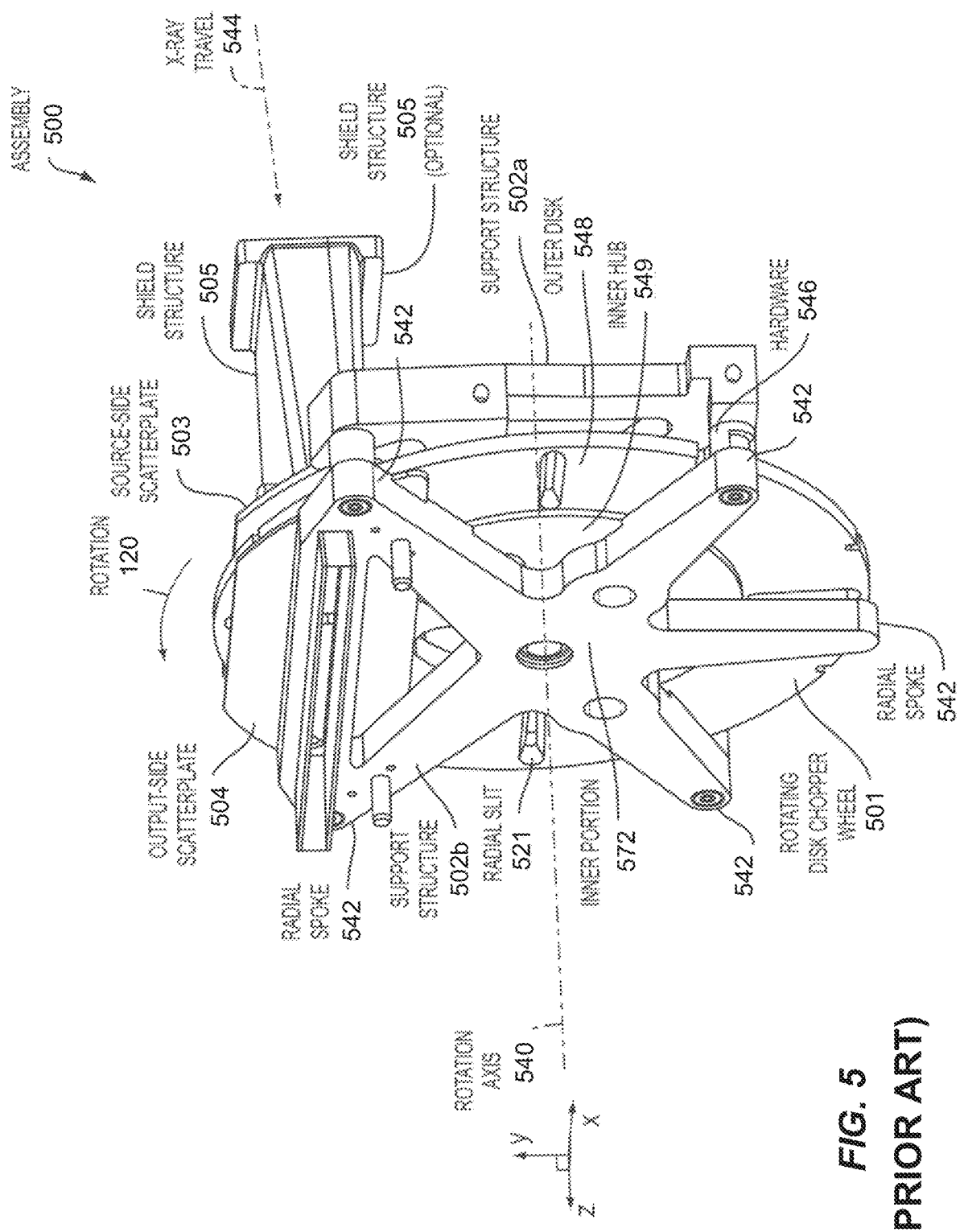
FIG. 5 (prior art) is a perspective-view illustration of an "open-geometry"-type disk chopper wheel assembly with scatter plates used in the prior-art Viken Detection™ handheld backscatter x-ray instruments.

FIG. 5 is a perspective-view illustration of an existing "open geometry" disk chopper wheel assembly 500 that includes scatter plates that has been used in previous Viken Detection™ handheld backscatter x-ray instruments, as described in U.S. Pat. Nos. 10,770,195 and 11,200,998. The assembly 500 includes a disk chopper wheel 501 that is configured to rotate about a rotation axis 540. In the illustration of FIG. 5, the rotation axis 540 coincides with the Z axis for the coordinate system that is shown. The rotation axis 540 is perpendicular to a rotation plane of the disk chopper wheel 501. The rotation plane is parallel to the XY plane that is shown in FIG. 5. The disk chopper wheel 501 has a solid cross-sectional area in the rotation plane. The wheel 501 is configured to absorb x-ray radiation traveling in a direction 544 from an x-ray source (not shown in FIG. 5) that is received at a source side of the chopper wheel (the side where x-rays are first incident, traveling along the direction 544). The disk chopper wheel 501 defines radial slit openings 521 around the wheel, and these radial slit openings are configured to pass x-ray radiation from the source side of the wheel to an output side of the disk chopper wheel.

The assembly 500 further includes a source-side scatter plate 503 that has a solid cross-sectional area in a plane parallel to the rotation plane of the wheel. The source-side scatter plate 503 is configured to absorb x-ray radiation, and it defines an open slot therein that is configured to pass x-ray radiation. Advantageously, the solid cross-sectional area of the source-side scatter plate is substantially smaller than the solid cross-sectional area of the disk chopper wheel, providing for operation of the assembly with significantly reduced weight, even while maintaining x-ray confinement similar to that of existing disk chopper wheel assemblies that include a full shielding enclosure surrounding an entire disk chopper wheel.

The source-side scatter plate 503 is secured by a support structure 502*a-b* that secures the source-side scatter plate substantially parallel to the rotation plane of the disk chopper wheel with a source-side gap between the source-side scatter plate and the source side of the disk chopper wheel. While an output-side scatter plate is generally optional, the assembly 500 does include an output-side scatter plate 504 that is secured by the support structure 502*a-b* to be substantially parallel to the rotation plane of the disk chopper wheel, similar to the source-side scatter plate 503. The support structure maintains an output-side gap between the output side of the scatter plate and the disk chopper wheel. In alternative assemblies not illustrated, the source-side and output-side scatter plates may form a single solid piece, the two scatter plates of which are connected by a bridge over the top of the disk chopper wheel 501 in FIG. 5. In alternatives, such a bridge structure may also be formed of a high-Z material to enhance shielding.

The output-side scatter plate 504 has a solid cross-sectional area in a plane parallel to the rotation plane of the disk chopper wheel. The output-side scatter plate is configured to absorb x-ray radiation, yet it also defines an open slot therein that is configured to pass x-ray radiation that emanates through the source-side scatter plate 503 and radial slits 521 in the chopper wheel. Advantageously, the solid cross-sectional area of the output-side scatter plate 504, like that of the input source-side scatter plate, is substantially smaller than the solid cross-sectional area of the disk, further providing for a lightweight assembly.

In the assembly 500, the support structure 502*a-b* is further configured to secure the disk chopper wheel 501 at the rotation axis 540. Advantageously, therefore, the support structure 502*a-b* performs both the functions of securing the chopper wheel and the functions of securing the source-side and output-side scatter plates 503 and 504, respectively. Further, in the assembly 500, it will be noted that the support structure includes the two portions 502*a* and 502*b* on the source side and output side of the chopper wheel, respectively. This provides a particularly robust and stable configuration that performs many needed support functions. However, in other assemblies, a support structure may be one-sided, and the chopper wheel and support structure may be secured and mounted separately, while still being secured with the source-side scatter plate being substantially parallel to the chopper wheel and having the appropriate gap between the source-side scatter plate and the source side of the chopper wheel.

Further in the assembly 500 in FIG. 5, the support structure 502*a*-502*b* includes an inner portion 572 that is configured to secure the disk chopper wheel 501 at the rotation axis 540 thereof, and the support structure 502*b* further includes radial spokes 542 that extend outward from the inner portion 572 and are configured to secure both the source-side scatter plate 503 and output-side scatter plate 504 with the appropriate alignment and gap with respect to the chopper wheel. The support structure 502*a-b* does this by means of hardware 546 that secures the two sides of the support structure 502*a* and 502*b* together while simultaneously securing the chopper wheel 501, as further illustrated in the exploded-view drawing of the assembly in FIG. 5. Accordingly, the source-side portion 502*a* and output side portion 502*b* of the support structure are configured to be connected together and to secure the disk chopper wheel between the two portions of the support structure.

The support structure 502*a-b* is formed of aluminum, advantageously, for lighter weight. In other embodiments, other materials may be used. Nonetheless, aluminum may be used advantageously because of low cost, sufficient rigidity and strength, and because the source-side and output-side scatter plates provide the desired shielding, while the support structure need not be relied upon for x-ray shielding.

The assembly 500 further includes an optional shield structure 505 that is configured to enclose the x-ray radiation in a region of travel between the x-ray source (e.g., x-ray tube, not shown in FIG. 5) and the source-side scatter plate 503. The shield structure 505 may be formed of a high-Z material, for example, such as tungsten, lead, iron, or another high-Z material having sufficient thickness to prevent incident or scattered x-rays from being emitted outside of the device.

Figure 6:
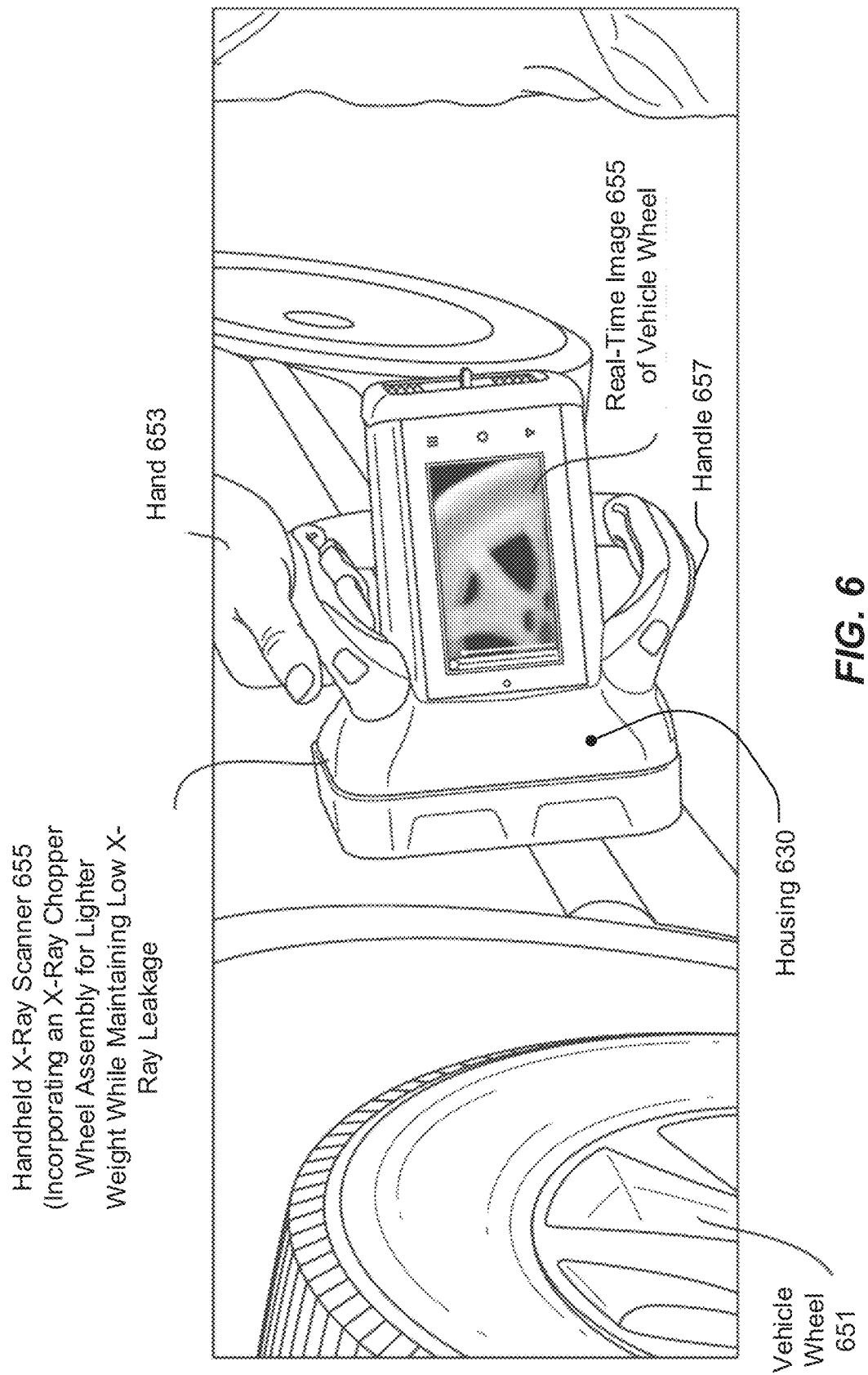
FIG. 6 (prior art) is an illustration of an existing handheld x-ray scanner incorporating an open geometry-type disk chopper wheel assembly of the type illustrated in FIG. 5.

FIG. 6 (prior art) is an illustration showing an existing handheld x-ray scanner 655 that incorporates an open-geometry-type x-ray disk chopper wheel assembly as shown in FIG. 5. Components of the scanner, such as an x-ray tube and the disk chopper wheel assembly 500 of FIG. 5, are mounted within a housing 659 of the handheld x-ray scanner 655. Various embodiment x-ray imaging apparatuses may be configured specifically for handheld operation, such as in FIG. 6. The scanner 655 can be carried and moved by a person via handles 657 to scan a vehicle, luggage, or other items flexibly to detect contraband, safety issues, etc.

As illustrated in FIG. 6, a hand 653 of a person holds the scanner 655, in this example via handles 657, and the scanner is directed at a vehicle wheel 651, an example target object for x-ray scanning for contraband. The x-ray scanner 655 is configured to produce a real-time image 655 of the vehicle wheel 651.

A disadvantage of using a disk chopper wheel in a handheld instrument is that the disk and associated shielding and collimators take up space and add substantial weight. Resolution is also limited for reasons described in connection with FIG. 13A.

Certain Embodiments within the Scope of the Present Claims, Drawings, and Description This application discloses novel hoop chopper wheel assemblies that can be used instead of a disk chopper wheel in a backscatter x-ray imaging instrument, and more particularly in handheld instruments but also in other types of instruments, such as robotically mounted or held or drone-mounted scanning applications, and even other scanning applications such as van-type or other vehicle mounted applications, cart-mounted applications, and transmission-imaging applications.

Figure 7:
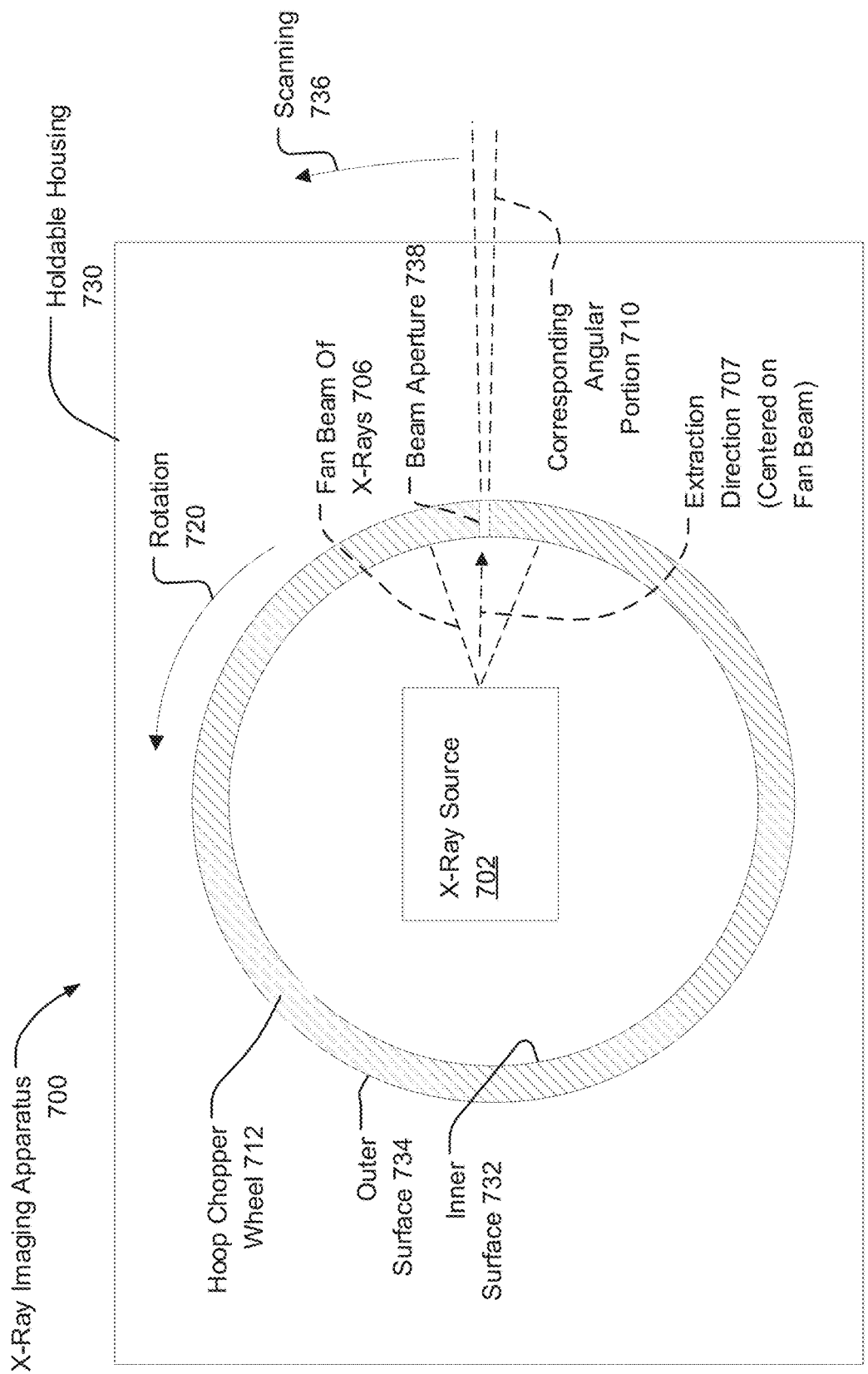
FIG. 7 is a schematic block diagram illustrating an x-ray imaging apparatus having a hoop-type chopper wheel consisting with present embodiments.

FIG. 7 is a block schematic diagram illustrating a generalized embodiment x-ray imaging apparatus 700. The apparatus 700 includes a holdable housing 730, a hoop chopper wheel 712, and an x-ray source 702. The x-ray source 702 is mounted within the holdable housing 730 and is configured to output a fan beam of x-rays 706. For convenience, it is noted that the fan beam 706 may be considered to have an extraction direction 707, defined as a center of the fan beam, as determined within a measurement tolerance or specified by a manufacturer, for example. The x-ray source may be a reflection-type x-ray tube, as illustrated in FIG. 30. Nonetheless, use of a transmission-type x-ray tube as the x-ray source 702 has significant advantages that will become further apparent in view of the totality of the the description and drawings.

The hoop chopper wheel 712 is rotatably mounted within the holdable housing 730 and it is formed of an x-ray attenuating material that is configured to block x-rays of the fan beam 706. Nonetheless, the hoop chopper wheel 712 also defines therein a set of beam apertures 738. As used herein, "set" denotes one or more. Each beam aperture of the set is configured to pass their through a corresponding angular portion 710 of x-rays from the fan beam 706. In this manner, rotation 720 of the hoop chopper wheel 712, which can be in the plane of the page through a center of the hoop chopper wheel 712 (not illustrated in FIG. 7) causes scanning of the corresponding angular portion 710 of x-rays, such as over the illustrated scanning direction 736. This is because, as the rotation 720 of the hoop chopper wheel 712 occurs, the corresponding angular portion 710 of the fan beam 706 that passes through the beam aperture 738 changes in direction over time.

It will be noted that the corresponding angular portion 710 of the x-rays should be understood to constitute a scanning pencil beam. The scanning pencil beam will naturally diverge with distance from the beam aperture 738, as illustrated. Thus, to maximize resolution as much as practical, it can be helpful to cause the scanning beam to intersect with a target object as near as possible to a position where the corresponding angular portion 710 exits that holdable housing 730. As described further hereinafter, embodiments provide significant benefits in resolution by enabling the noted distance to be decreased.

Also illustrated in FIG. 7 is an example inner surface 732 and an example outer surface 734 of the hoop chopper wheel 712. These surfaces are depicted in FIG. 7 as being circular, smooth, and concentric for simplicity and convenience only. Nonetheless, in various embodiments, it should be understood that the outer surface 734 can have flat or other non-circular facets. Furthermore, the hoop chopper wheel 712 may be formed of segments that are configured to be attached together. Moreover, the hoop chopper wheel 712 may have features such as additional drilled holes, added weights, or other features useful for balancing the wheel during rotation. Various other features that are optional for the hoop chopper wheel 712 will become apparent further throughout the remaining description.

FIG. 8 is a perspective-view diagram illustrating a scanning module with an in-line hoop chopper wheel 812 that may be used in the present x-ray imaging apparatus embodiments. The inner surface of the narrow rotating hoop 812 of x-ray attenuating material such as tungsten is irradiated by a fan beam 806 output from an x-ray source, specifically a transmission-type x-ray tube 802. The fan beam 806 is output in substantially the same plane as a plane of rotation of the hoop chopper wheel 812, centered vertically to irradiate a set of apertures 838. The apertures 838 defined in the hoop chopper wheel 812 allow some of the x-rays in the fan beam 806 to pass therethrough, creating a sweeping pencil beam of x-rays 810 that sweeps from side to side as the hoop rotates about the source. The apertures can be circular, ellipsoidal, or rectangular slits, as just a few examples. A high-voltage power supply 840 is included in order to power the tube with the high voltage necessary to accelerate electrons and produce x-ray radiation.

FIG. 9 is a perspective-view diagram illustrating the scanning module of FIG. 8 that may be used in present embodiments, along with an example placement of backscatter detectors 938 relative to a hoop chopper wheel 812. FIG. 9 illustrates a significant advantage of using a hoop chopper wheel, especially for holdable embodiments. Namely, the hoop 812 can be made narrow enough so that the irradiated apertures 838 within the hoop can be located very close to a front of a housing that houses the tube 802 and hoop 812, adjacent to the detectors 938, without interfering with a backscatter detector assembly. This is illustrated further in FIG. 12. This means that a beam width at the point that the beam exits the front of the instrument is almost identical to the aperture width, resulting in much higher resolution than can be achieved with the disk chopper assembly set back into the instrument. This advantage of hoop-based embodiments is made more clear in FIG. 10 and in FIGS. 13A-13B, for example.

FIG. 10 shows computer-simulated backscatter images of a line-pair phantom acquired with a prior-art Viken Detection™ HBI™ handheld x-ray scanner with a disk chopper wheel (upper image) compared to images acquired with embodiment hoop-type chopper assemblies with 1.0 mm square and 0.5 mm×10 mm rectangular apertures (middle and lower images, respectively). In FIG. 10, simulated backscatter x-ray images of a line pair phantom are shown for the prior-art HBI-120™ system (top image) with the chopper disk assembly shown in FIG. 6 compared with images obtained with a system with a hoop chopper assembly as shown in FIG. 9, with 1 mm square apertures (middle image) and 0.5 mm×1.0 mm rectangular apertures (bottom image). It is readily apparent from FIG. 10 that the images obtained with the embodiment hoop chopper assembly apparatus can have much higher resolution than for the prior-art system, which has the disk chopper wheel assembly.

While the embodiment of the hoop chopper assembly shown in FIG. 9 produces high-resolution images, the diameter of the hoop must be large enough in that particular embodiment to allow the hoop to rotate without interfering with the x-ray tube. For some holdable apparatuses such as handheld instruments, this can require using a hoop with a diameter of approximately 5 inches, which can make it challenging to package the chopper assembly into a compact, light-weight handheld instrument.

Figure 11:
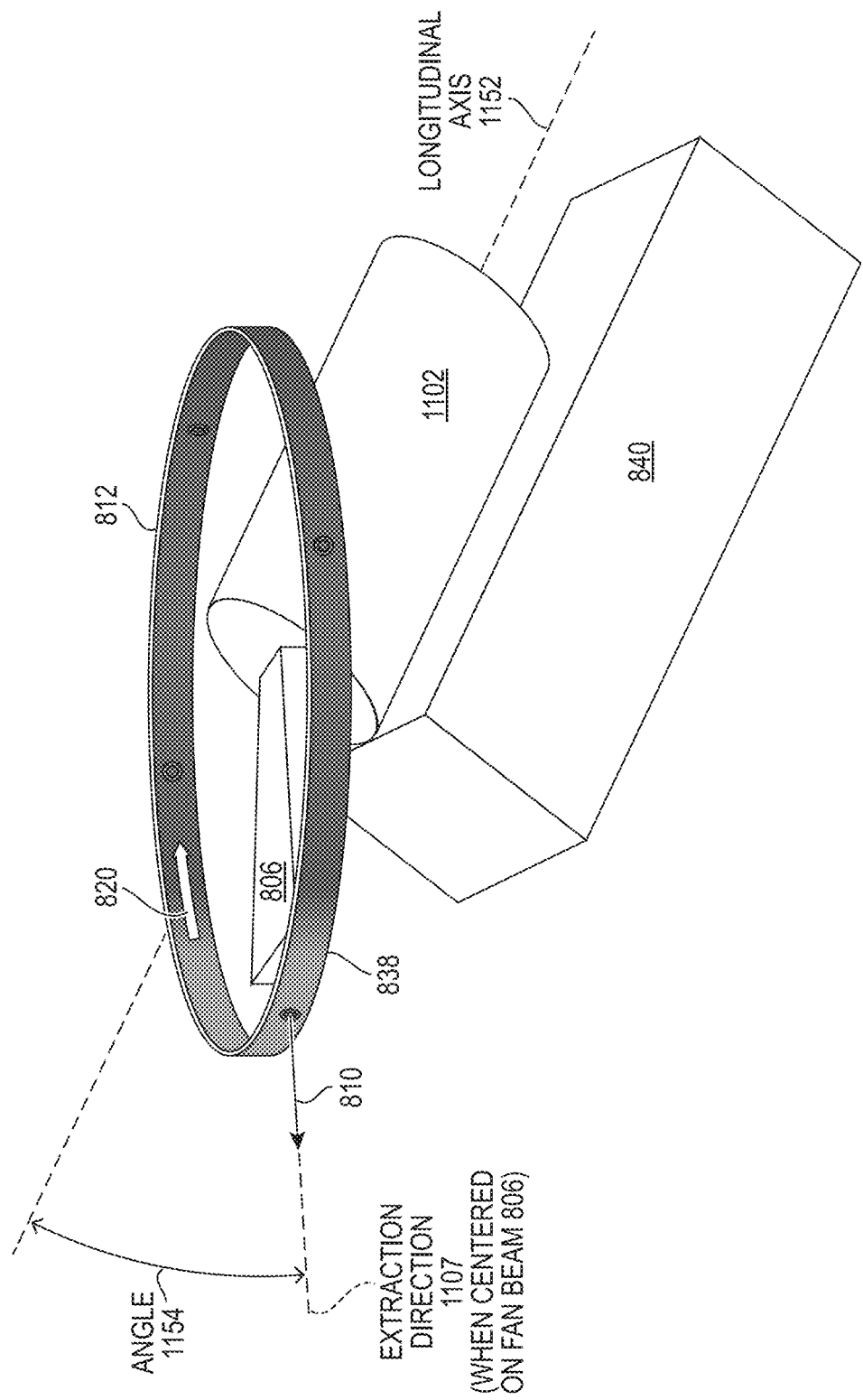
FIG. 11 is a perspective-view diagram illustrating a scanning module with an "angled tube" configuration that is particularly advantageous in embodiments.

FIG. 11 illustrates how in one preferred embodiment, the fan beam emitted from the x-ray source transmission anode can be extracted in an extraction direction 1107 that forms an angle 1154 with respect to the long axis of the x-ray tube (for example, 45 degrees). The angle can be generally greater than 0 degrees, between 0 and 90 degrees, in a range of about 10 degrees to about 60 degrees, in a range of about 20 degrees to about 50 degrees, in a range of about 25 degrees to about 35 degrees, or in a range of about 25 degrees to about 35 degrees. In this context, "about" means to within a measurement tolerance for the angle. This can allow a smaller diameter hoop to be used, as shown in the example of FIG. 11. Specifically, FIG. 11 is a perspective-view diagram illustrating a scanning module with an "angled tube" configuration that is particularly advantageous in embodiments. In this embodiment (called the "angled tube" configuration), the hoop does not have to clear the entire length of the x-ray tube, allowing a considerably smaller hoop of approximately 3 inches diameter to be used. This makes it much easier to design the hoop into a compact footprint and saves considerable weight. The "long axis" of an x-ray tube, as used herein, is specifically the longitudinal axis 1152, which is the axis over which electrons are accelerated toward the anode of the tube to generate x-rays.

Figure 12:
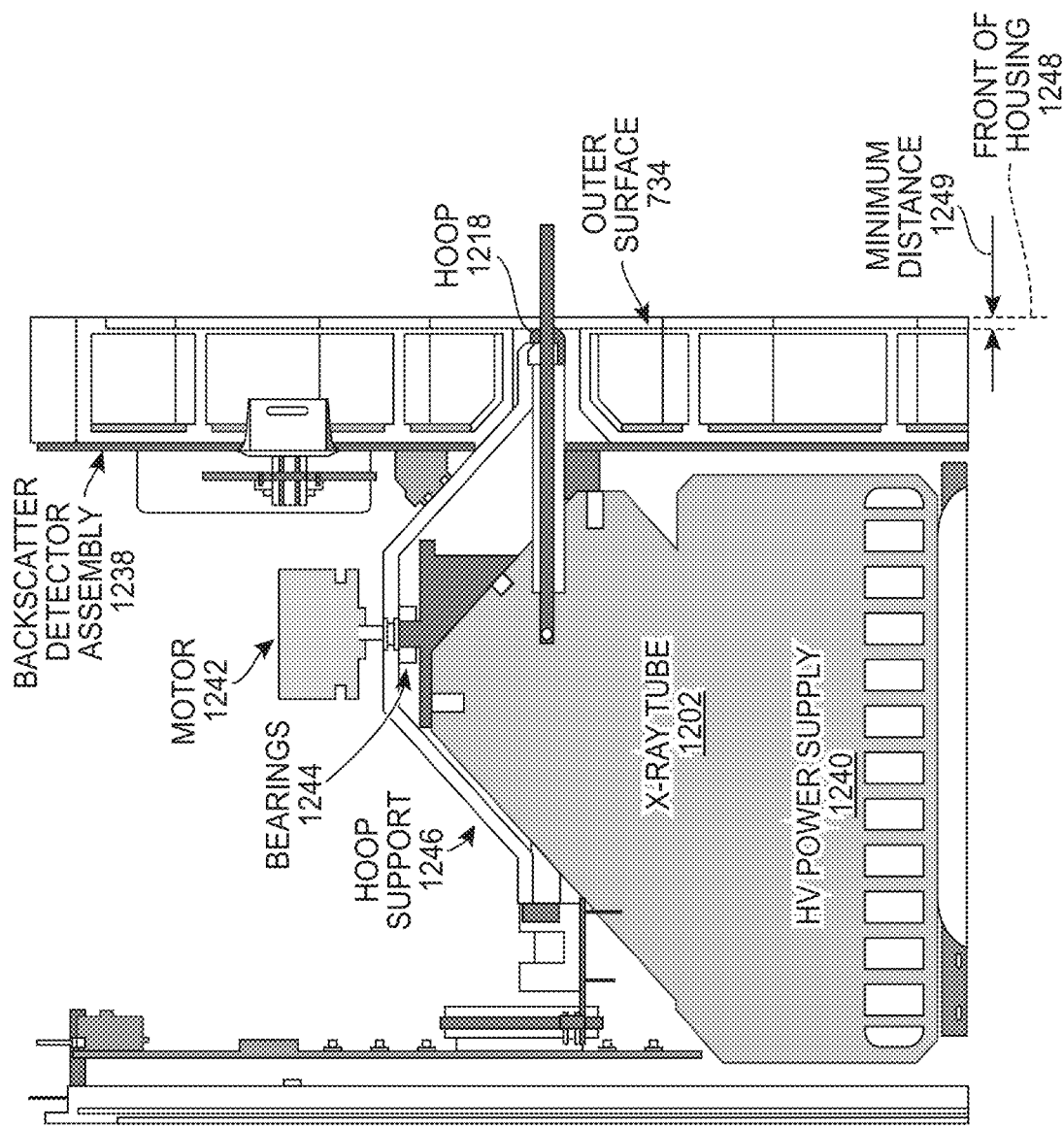
FIG. 12 is a profile-view diagram illustrating an component layout in embodiment x-ray scanning module that has an "angled tube" configuration and is configured to be handheld.

FIG. 12 shows an example of packaging such a hoop chopper wheel in a handheld instrument is shown in FIG. 12. Specifically, FIG. 12 is a profile-view diagram illustrating an component layout in embodiment x-ray scanning module that has an "angled tube" configuration and is configured to be handheld A tungsten hoop 1218, about 5 mm wide and 3 mm thick and defining circular or rectangular beam apertures, is supported by an aluminum cup hoop support 1246 that is mounted onto a shaft supported by dual bearings 1244 and driven by a small electric motor 1242. The bearings 1244 can be mounted firmly to the x-ray source (tube) 1202 to ensure accurate alignment of the fan beam and hoop apertures. This is one example that illustrates how, in embodiments, a minimum distance 1249 between an outer surface of the hoop chopper wheel and a front of the apparatus housing 1248 can be made very small in order to enhance possible resolution. The minimum distance is measured from the front of the housing 1248 to the nearest point of the outer surface of the hoop chopper wheel. In other words, the distance 1249 may be considered as from an outer surface of the hoop chopper wheel adjacent to an aperture that is irradiated at a given time, to a front of the housing that may abut an external target object during a scan. The minimum distance in various embodiments can be less than about 50 mm, less than about 30 mm, less than about 10 mm, less than about 5 mm or between about 10 mm and about 1 mm. "About" in this context means within tolerance of measurement accuracy.

Figure 13A:
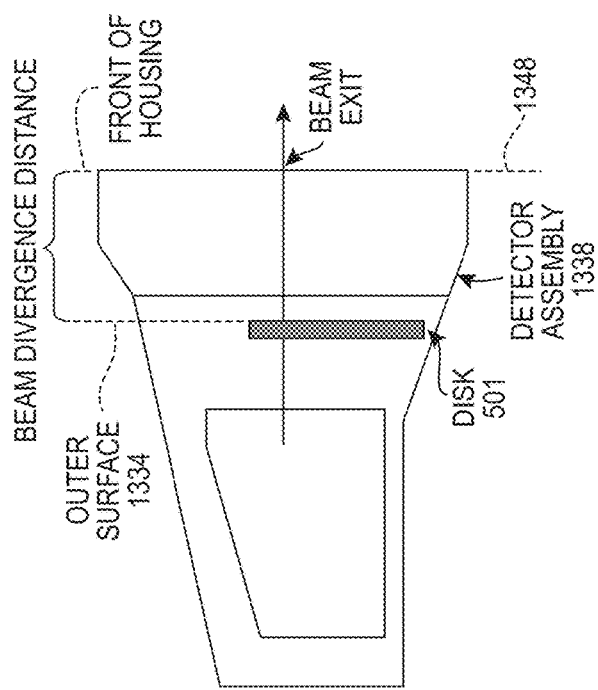
FIG. 13A (prior art) is a profile-view illustration of an existing Viken Detection™ HBI™ x-ray scanning instrument showing distance between a disk chopper wheel therein and a front of a housing of the instrument.
Figure 13B:
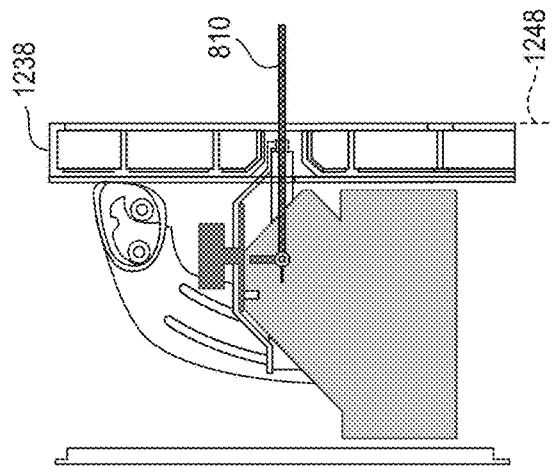
FIG. 13B is a profile-view diagram illustrating an embodiment x-ray scanning apparatus for comparison with FIG. 13A, illustrating in FIG. 13B how embodiments facilitate having a focal spot of a x-ray scanning beam much closer to an output of the whole instrument for improved resolution.

Referring further to FIGS. 13A-13B, the advantages of an instrument containing this embodiment of the hoop chopper assembly (lower image) compared with a prior-art Viken Detection™ handheld backscatter x-ray instrument with the normally irradiated chopper disk (upper image) are apparent. As noted above, a disadvantage of using a disk chopper wheel in a handheld instrument is that the disk and associated shielding and collimators take up quite a lot of space and add substantial weight. The weight typically must be borne by the operator, often for extended periods of time. As an example, the chopper disk and associated pre-collimator and post-collimator shielding in the Viken Detection™ HBI-120™ system weighs about 1.2 lbs. Another disadvantage of using a disk chopper wheel is that, due to its size and highly attenuating materials, the disk must be installed behind the backscatter detector assembly, as illustrated in FIG. 13A for the Viken HBI-120™ instrument. This typically requires the disk chopper wheel 501 to be installed with an outer surface 1334 thereof to be at least one inch (and usually much more) behind the front face 1348 of the instrument's housing. Due to the divergence of the pencil beam as it exits the chopper disk assembly, the beam is substantially wider than the slit apertures in the disk by the time the beam exits the front of the instrument. Since the imaging resolution of the instrument is defined by the width of the beam at the point it irradiates the target object, the image resolution is degraded compared to what could be achieved if the disk were located right at the front of the instrument, and not located behind the backscatter detectors. Weight and potential resolution are also a significant issues for small robots and drones to which an x-ray scanning apparatus may be mounted for remote inspection of possibly dangerous items. Thus, this is an important issue facing a variety of holdable x-ray scanning tools.

Using the embodiment apparatus of FIG. 13B, the length of the handheld imager (in the center direction of the scanning pencil beam emission 810) is greatly reduced compared with FIG. 13A, allowing the embodiment imager apparatus of FIG. 13B to be inserted into much smaller spaces. For example, the length of the instrument would now be short enough to allow the undercarriage of cars with even very small ground clearance to be scanned.

Regarding weight reduction, the disk chopper assembly of the prior-art Viken Detection™ handheld instruments weighs approximately 1.2 lbs while the hoop chopper assembly (with the "angled tube configuration") would weigh a little under 0.5 lbs, resulting in a weight savings of 0.7 lbs. This is a substantial weight reduction for a handheld instrument.

Figure 14:
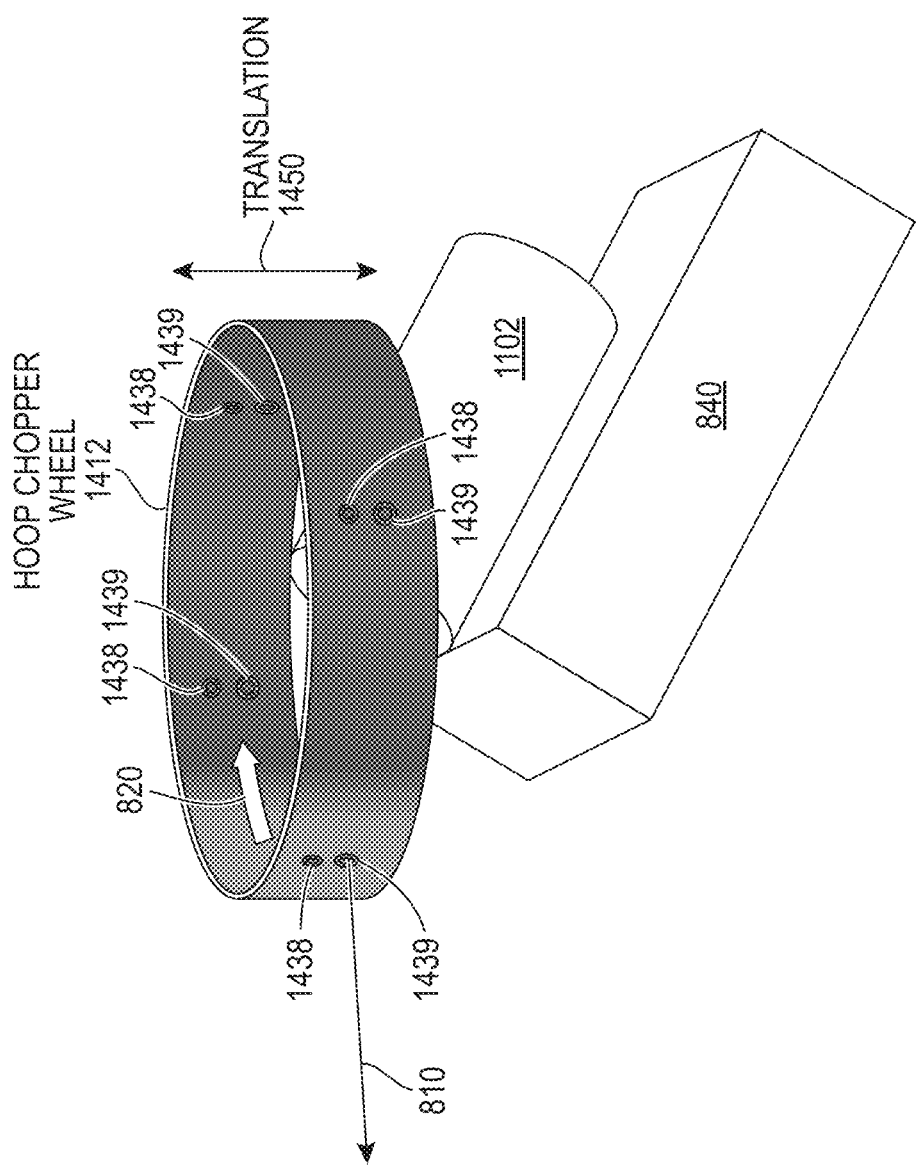
FIG. 14 is a perspective-view diagram illustrating a scanning module that may be used in embodiments having two subsets of beam apertures that can be translated relative to the x-ray source for selectable scanning resolution.

FIG. 14 is a perspective-view diagram illustrating a scanning module with a variable resolution hoop chopper wheel 1412 that may be used in embodiment apparatuses. The module has two subsets of beam apertures 1438, 1439 that can be translated with a translation 1450 relative to the x-ray source 1102. This enables selectable scanning resolution, since the subsets 1438, 1439 have different aperture sizes.

A further embodiment of the hoop chopper wheel assembly can allow an entire hoop and supporting cup assembly to be raised with an actuator into two or more positions. This can allow two or more subsets of apertures in the hoop to be irradiated selectively by the incident fan beam. For example, one subset of smaller apertures can be used for optimized high-resolution imaging, and another subset of larger apertures can be used for optimized higher-penetration (lower resolution) imaging.

Figure 15:
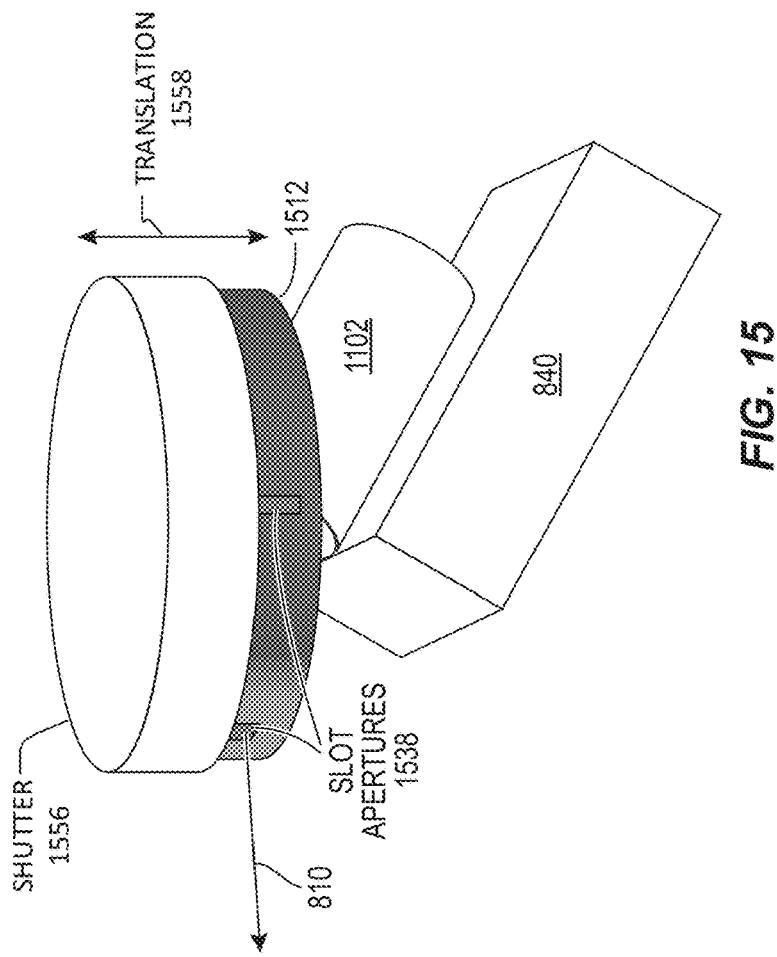
FIG. 15 is a perspective-view diagram illustrating a scanning module that may be used in embodiments having a single set of elongated slot-type beam apertures, and an additional non-rotating barrel that can be used to adjust, selectively, the size of the apertures in one dimension.

FIG. 15 is a perspective-view diagram illustrating a scanning module that may be used in embodiments having a single set of elongated slot-type beam apertures 1538, and an additional non-rotating barrel-shaped shutter 1556 that can be used to adjust, selectively, the size of the slot apertures 1538 in one dimension. This is done in this embodiment via a translation 1558 of the barrel-type shutter 1556.

Figure 16:
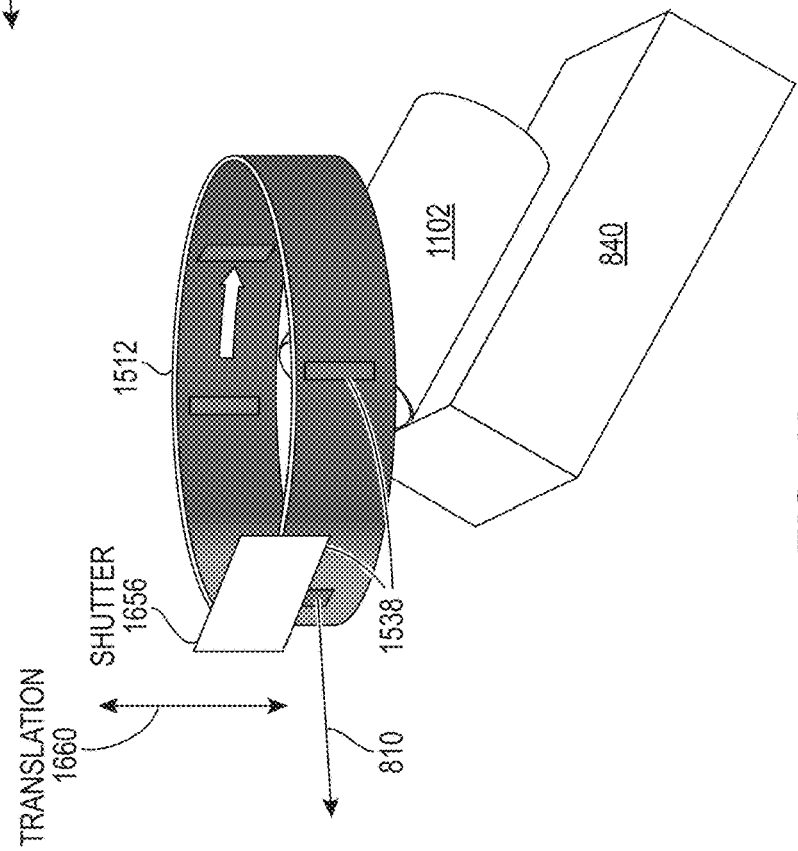
FIG. 16 is a perspective-view diagram illustrating a scanning module with a single set of elongated beam apertures, and a translatable shutter edge that can be used to adjust, selectively, the size of the apertures in one dimension.

FIG. 16, like FIG. 15, has only the single set of the elongated, slot-type beam apertures 1538. In the perspective-view diagram of FIG. 16, the elongated beam apertures are provided with adjustable size, for adjustable instrument resolution, via translation 1660 of a translatable shutter 1656. Movement of the bottom edge of the shutter 1656 is used to control size of the apertures 1538. Either embodiment of FIG. 15 or FIG. 16 can allow resolution and/or penetration to be selected for a given imaging application.

Figure 17:
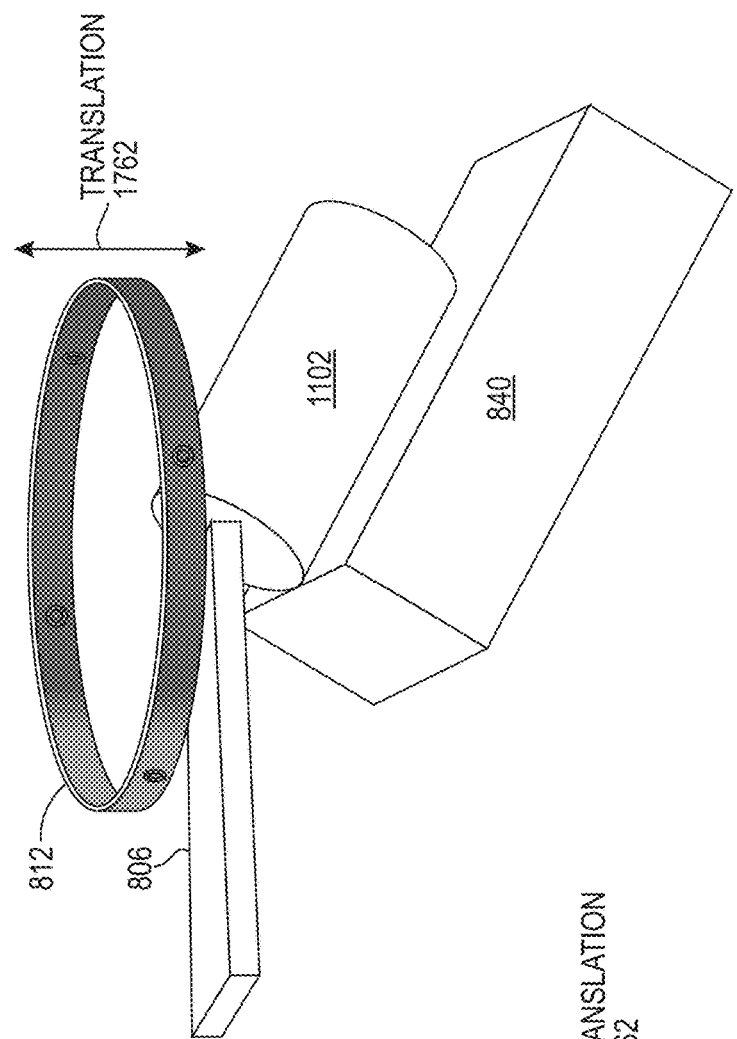
FIG. 17 is a perspective-view diagram illustrating a scanning module having a hoop chopper wheel that can be translated out of a plane of the incident fan beam, allowing emission of a fan beam rather than a sweeping pencil beam, which can be useful in embodiments.

FIG. 17 is a perspective-view diagram illustrating a scanning module having the hoop chopper wheel 812 movable by at translation 1762 (out of a plane of the incident fan beam 806). This allows output of the fan beam 806 from the apparatus rather than the sweeping pencil beam 810. This can be useful in various embodiments including for holdable x-ray scanning apparatuses that can benefit from both types of output beams from the same unit, selectively. In one example, a fan beam can be emitted from the apparatus for use with a segmented linear detector array, or alternatively, with a two-dimensional pixelated panel detector. Then the pencil beam output can be selected for backscatter imaging.

Figure 18:
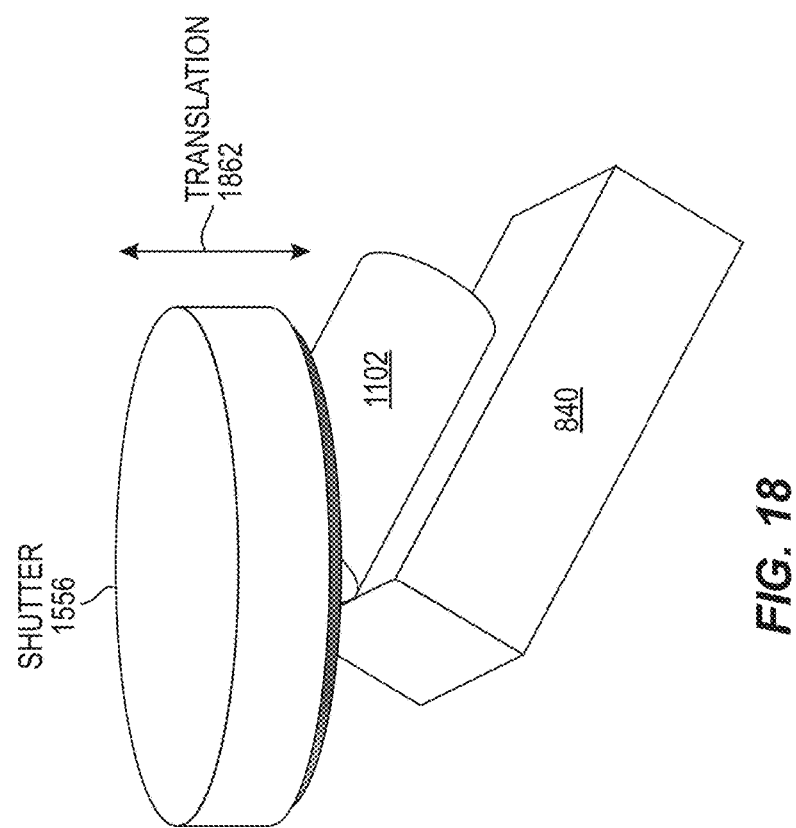
FIG. 18 is a perspective-view diagram illustrating a scanning module with a non-rotating barrel that can be used to act as a selective shutter mechanism to prevent emission of radiation during source warmup, which can be useful in embodiments.

FIG. 18 is a perspective-view diagram illustrating a scanning module that can be used in embodiments. The module includes the non-rotating barrel-type shutter 1556 of FIG. 15. Via a translation 1862, the shutter 1556 can be used to act as a selective shutter mechanism to prevent emission of radiation during warmup of the x-ray source 1102.

Figure 19:
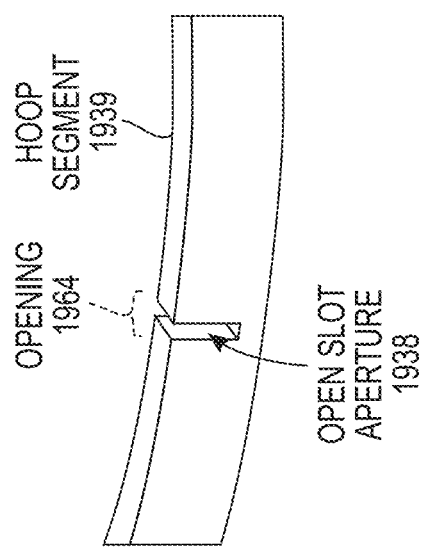
FIG. 19 is a perspective-view illustration of a segment of a hoop chopper wheel that has rectangular slotted beam apertures open at one end, which can be useful in embodiments.

FIG. 19 is a perspective-view illustration of a hoop segment 1939 of a hoop chopper wheel (not shown in its entirety in FIG. 19. The embodiment of FIG. 19 includes rectangular slotted beam apertures 1938 that are open at one end (see an example opening 1964). A full hoop chopper wheel can be constructed of many such hoop segments 1939 where the segments are configured to be attached to one another.

A yet further embodiment can move the rotating hoop completely out of the plane of the fan beam. In a further embodiment, the rotating hoop can be moved so that the apertures are no longer in the plane of the fan beam, effectively allowing the hoop to act as a shutter and turning off the beam emitted by the instrument all together. This can be useful during the warmup period for the x-ray source, when it is desirable to have the source energized at increasing levels of output, without the safety concerns of an emitted beam during these periods. A further embodiment to achieve this includes an additional inner or outer non-rotating hoop or barrel which can be positioned to block the apertures in the hoop, acting as a shutter to prevent any radiation from being emitted by the system (FIG. 18). It will be clear to those of ordinary skill in the art in view of this disclosure that the embodiment shown in FIG. 15 can also be used to achieve the configuration shown in FIG. 18.

A further embodiment uses one or more lasers placed within the collimation path between the x-ray source and the rotating hoop (preferably as close to the focal spot of the x-ray source as possible), so that the laser light can irradiate the object being imaged through the beam apertures, providing a precise visual indicator to the operator of where the x-ray beam is irradiating the object at any given time. The one or more lasers are placed close to the focal spot, but to one or both sides to prevent any attenuation of the x-ray beam.

Figure 20:
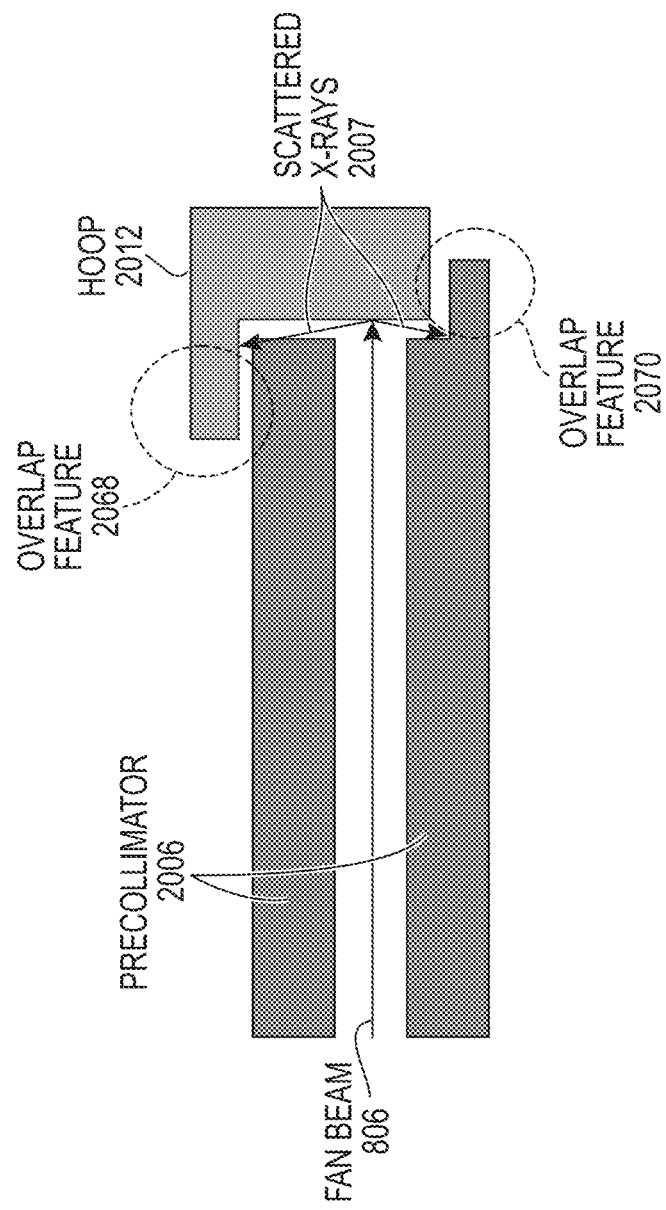
FIG. 20 is a cross-sectional-view diagram of a hoop chopper wheel and pre-collimator assembly incorporating features to reduce leakage at their interface, which can be useful in embodiments.

FIG. 20 is a cross-sectional-view diagram of a hoop chopper wheel and pre-collimator assembly incorporating features to reduce leakage at their interface, which can be useful in embodiments. In this example, a hoop 2012 has an overlap feature 2068. A precollimator 2066 further has an overlap feature 2070. Both 2068 and 2070 work to decrease any leakage of scattered x-ray 2007 that are from the fan beam 806 and are scattered from the hoop 2012 or precollimator 2066.

Various embodiments can use a slotted hoop with one or both ends being open, as shown in the exemplification in FIG. 19, or can advantageously use features incorporated onto the rotating hoop and/or pre-collimator assembly to prevent x-ray scatter from leaking from the interface between the pre-collimator assembly and the hoop, as shown in the exemplification of FIG. 20.

Figure 21:
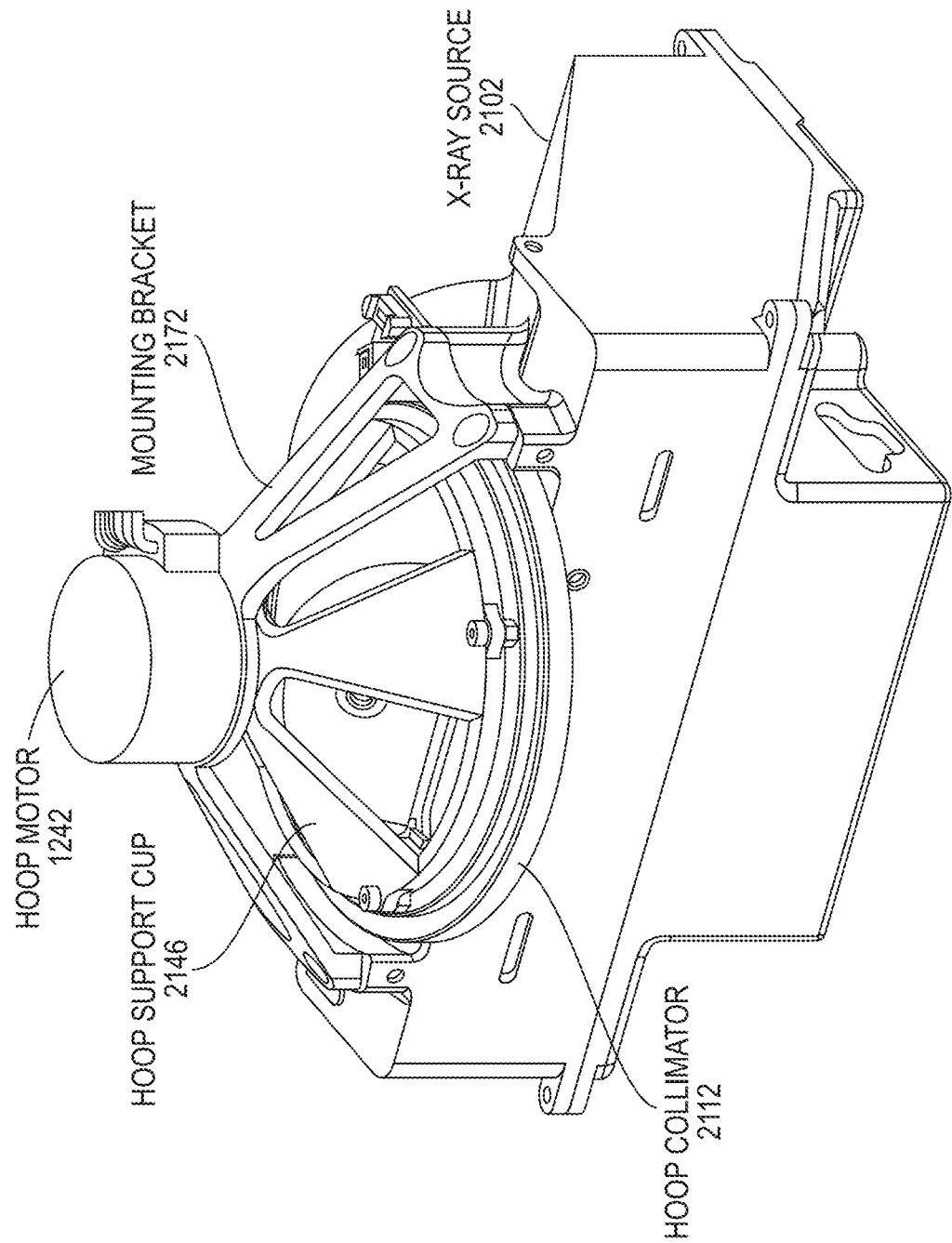
FIG. 21 is a perspective diagram of an embodiment x-ray scanning apparatus having a hoop collimator and a cup-type hoop support.

FIG. 21 is a perspective diagram of an embodiment x-ray scanning apparatus having a hoop collimator 2112 and a cup-type hoop support 2146 mounted to a mounting bracket 2172. Other embodiments include a plate-type hoop support or another type of hoop support. An x-ray source 2102 (transmission-type) is also used in the apparatus).

Figure 22:
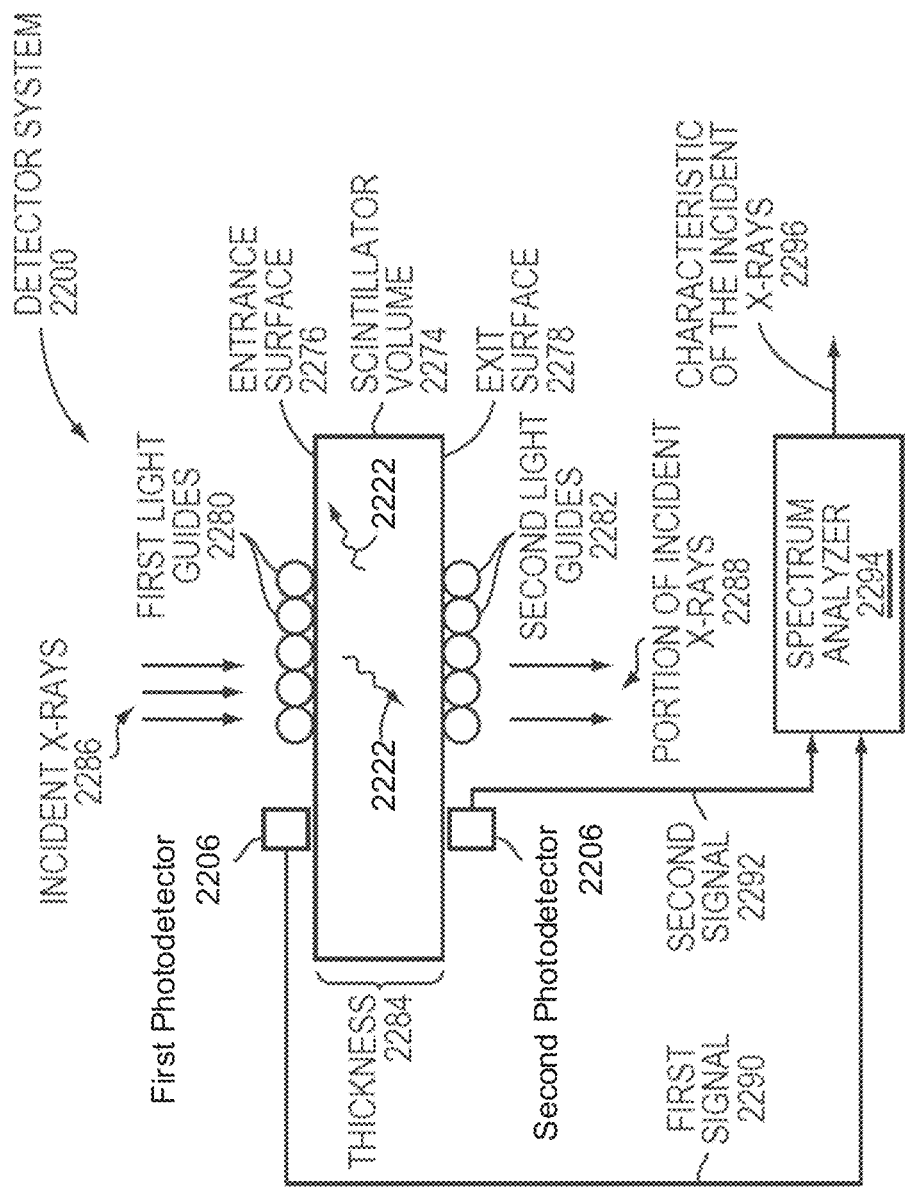
FIG. 22 is a schematic illustration of a detector system, for determining a characteristic of an energy spectrum of x-rays, which may be used in embodiments.

FIG. 22. FIG. 22 is a schematic illustration of a detector system 2200, for determining a characteristic of an energy spectrum of x-rays, which may be used in embodiments. The detector system 2200 includes a scintillator volume 2274 having an entrance surface 2276 and an exit surface 2278. The entrance surface 2276 is configured to receive incident x-rays 2286. The incident x-rays 2286 may be from a scanning x-ray beam, also referred to herein as a sweeping x-ray beam, a stationary x-ray beam, such as a cone beam, or a fan beam, which have been transmitted through a target object, for example. Alternatively, the incident x-rays 2286 may be backscattered x-rays that are backscattered from a target.

The scintillator volume 2274 is configured to emit scintillation light 2222 responsive to receiving the incident x-rays 2286. The exit surface 2278 is configured to pass a portion of the incident x-rays 2286 that traverse a thickness 2284 of the scintillator volume 2274 between the entrance surface 2276 and the exit surface 2278.

The detector system 2200 further includes a first plurality of light guides 2280 that are optically coupled to the entrance surface 2276 of the scintillator volume 2274. The system 2200 also includes a second plurality of light guides 2282 that are optically coupled to the exit surface 2278 of the scintillator volume 2274.

The system includes at least one first photodetector 2206 that is optically coupled to an end of the first light guides 2280. The first photodetector is configured to output a first signal 2290 responsive to the scintillation light 2222 from the scintillator volume 2274. The system also includes at least one second photodetector 2208 that is optically coupled to an end of the second plurality of light guides 2282 and is configured to output a second signal 2292 responsive to the scintillation light 2222 from the scintillator volume 2274. Although ends of the first and second light guides are not specifically illustrated in FIG. 22, it will be understood that in the case when the light guides are wavelength shifting fibers (WSFs), the ends of the light guides are ends of the WSFs.

The detector system 2200 further includes a spectrum analyzer 2294 that is configured to receive the first and second signals 2290, 2292 responsive to the scintillation light and to determine a characteristic of an energy spectrum a characteristic 2296 of an energy spectrum of the incident x-rays 2286 based on the first and second signals 2290, 2292.

The characteristic 2296 can include, for example, relative signal strength for at least two different wavelength segments of an energy spectrum of the incident x-rays 2286, for example. The characteristic 2296 alternatively can include an indication of a material or a material class of a target object through which the incident x-rays 2286 pass, or from which the incident x-rays 2286 are scattered. Identification of a material or material class of the target, or of other characteristics 2296 of incident x-rays incident on a dual energy x-ray detector, are known to those of skill in the art and are within the scope of this disclosure. However, such characteristics have not been previously determined with the benefit of a detector system such as the detector system 2200, which takes advantage of a single, common scintillator volume 2274 and relies on self-attenuation of scintillation light within the scintillator volume 2274 in order to achieve energy discrimination in the manner illustrated and described.

The spectrum analyzer may be a computer processor or an embedded processor or the like. It may output the characteristic of the energy spectrum, directly or indirectly, to a communication interface, a display, a printout, a human, etc.

The thickness of the scintillator volume can be larger than a self-attenuation length of a scintillator material of the scintillator volume. The scintillator volume can be a strip scintillator volume configured to receive the incident x-rays at the entrance surface thereof, from a sweeping x-ray beam transmitted through a target, over a sweep of the sweeping x-ray beam. The scintillator volume can be an area scintillator volume, for example. The scintillator volume may be configured to receive the incident x-rays at the entrance surface via x-ray scattering from a target object. However, incident x-rays may alternatively be received at the entrance surface via passive emission from a target.

The first and second pluralities of light guides can be wavelength-shifting fibers (WSFs) or other light guides.

The scintillator volume can be in a tubular form, for example. The entrance and exit surfaces can be outer and inner curved surfaces, respectively, of a tubular wall of the scintillator volume if the volume defines an inner hollow portion. The first and second pluralities of light guides can be first and second pluralities of ribbons of WSFs, respectively, covering the outer and inner curved surfaces, respectively, of the tubular wall. The first plurality of ribbons can be wrapped around the outer curved surface in a spatially periodic, substantially helical pattern. The second plurality of ribbons can be inlaid around and adjacent to the inner curved surface in a repeating, spatially periodic, substantially helical pattern.

The at least one first photodetector and the at least one second photodetector can be photomultiplier tubes (PMTs). The at least one first photodetector and the at least one second photodetector can be separate anodes of at least one multi-anode PMT.

A scintillator material of the scintillator volume can include one or more materials selected from a group consisting of BaFCl, GOS, YOS, and ZnS.

Figure 23:
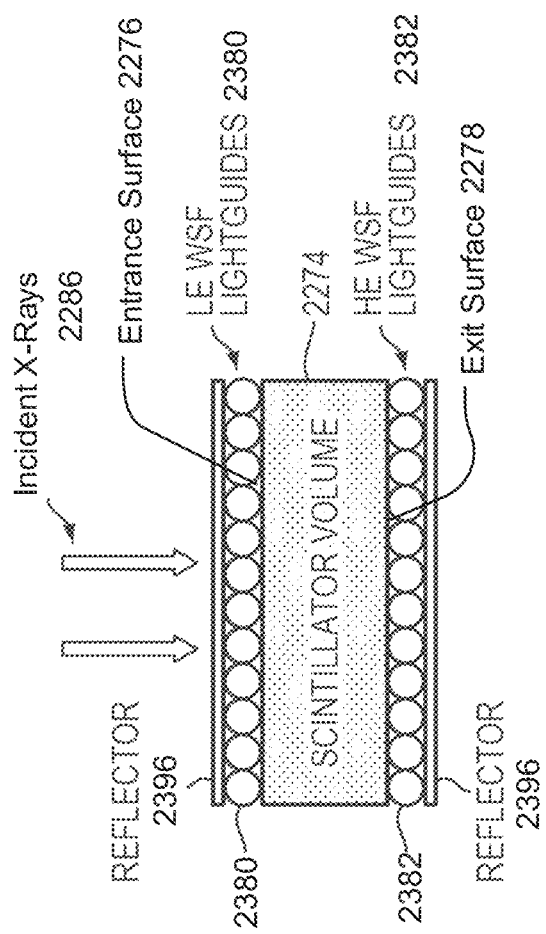
FIG. 23 is cross-sectional view illustration of certain components of a detector system that may be used in embodiments, showing a scintillator volume used for both low-energy and high-energy channels in accordance with a preferred embodiment, with a central region of the detector, the scintillator volume, acting as a virtual filter (also referred to herein as an "effective self-filter") for enhancing energy discrimination.

FIG. 23 is cross-sectional view illustration of certain components of a detector system that may be used in embodiments, showing a scintillator volume used for both low-energy and high-energy channels in accordance with a preferred embodiment, with a central region of the detector, the scintillator volume, acting as a virtual filter (also referred to herein as an "effective self-filter") for enhancing energy discrimination.

FIG. 23 is a cross-sectional view of an advantageous embodiment configured specifically for x-ray transmission imaging. One volume of scintillator 2274 is advantageously used for both the low-energy detector channel 2380 and the high-energy channel 2382. The low-energy x-rays are preferentially absorbed closer to the entrance surface 2276 of the scintillator volume 2274, with the resulting scintillation light preferentially entering the layer of WSF 2380 optically coupled to the entrance surface of the scintillator volume 2274. The higher-energy x-rays, which are more penetrating, will be absorbed, on average, deeper in the scintillator medium volume 2274, and the resulting scintillation light will preferentially enter the HE layer of WSF 2382 optically coupled to the exit surface 2278 of the scintillator volume 2274.

A reflector 2396 (top) assists to optically couple scintillation light produced by lower-energy x-rays by reflecting such light back toward the layer 2380. Similarly, a reflector 2396 (bottom) assists to optically couple scintillation light produced by higher-energy x-rays by reflecting such light back toward the layer 2382.

Figure 24:
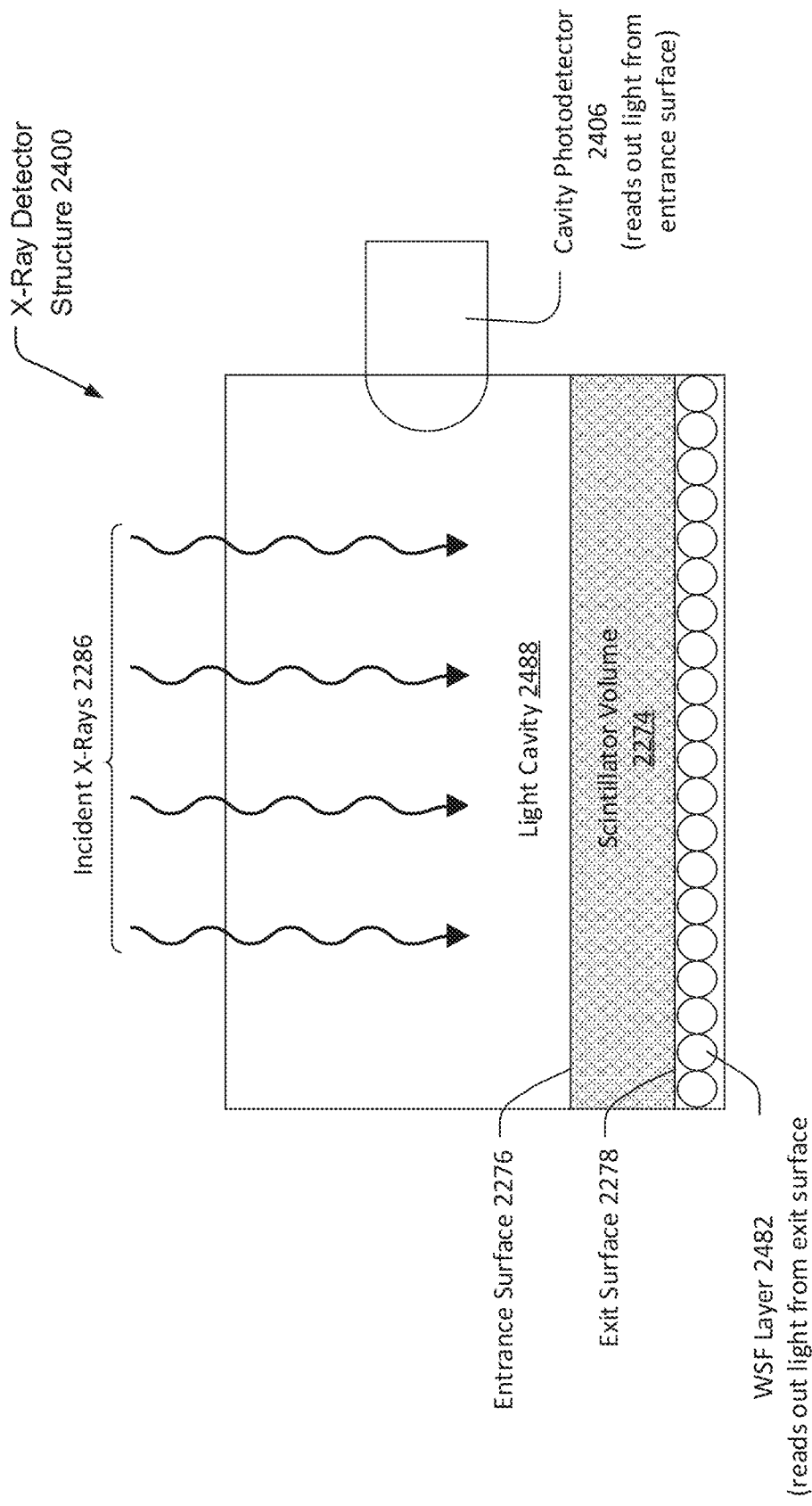
FIG. 24 is a schematic illustration of an alternative detector structure that may be particularly advantageous in embodiments, in which a light cavity take the place of the first layer of wavelength shifting fibers (WSFs).

The energy discrimination characteristics of the detector system shown in FIG. 22, and the detector structures of FIGS. 23-24, for example, can be optimized by carefully selecting the scintillator medium according to the following criteria:

Scintillator medium composition
Scintillator thickness
Scintillator optical attenuation The scintillator medium and thickness can be carefully selected to ensure that the detection efficiency of the high-energy x-rays is high, while ensuring that the mean absorption depth of the x-rays in the low-energy and high-energy regions are well separated, providing good discrimination in the amount of scintillation light collected in the two independent WSF layers. This can be further enhanced by ensuring that the mean-free-path of the scintillation light in the scintillation medium is relatively short. This ensures that the light from the low-energy x-rays (absorbed near the entrance surface) has a low probability of being absorbed in the WSF layer on the exit surface, and conversely, that the light from the higher-energy x-rays (absorbed closer to the exit surface) has a lower probability of being absorbed in the WSF layer on the entrance surface.

A preferred scintillator medium that is relatively low cost and easy to incorporate mechanically into larger detectors is scintillating phosphor screen, such as BaFCl. This particular phosphor has a peak scintillation wavelength of about 390 nm, which is ideally matched to the peak absorption spectra of many types of WSF. It has a high detection efficiency for x-rays in the energy range of 25 keV to 225 keV and because of its crystalline structure, it has a relatively short mean-free-path of less than a millimeter for self-absorption of its own scintillation light, enhancing the separation in light collection between the two layers of WSF for low-energy versus high-energy x-rays.

By optimizing the thickness and optical light attenuation characteristics of the scintillator medium, a "dead" zone at the center of the scintillator volume can be established, for which scintillation light cannot reach either layer of WSF. The scintillator material in this center zone is therefore now acting effectively as a filter, as light from this region is not able to be detected at all. The only effect of this center material is to absorb or filter the higher energy x-rays that can pass into the high-energy region of the scintillator and contribute to the HE channel signal. This "dead" zone can therefore be optimized to further enhance the energy discrimination capability of the detector. In one example, a 500 mg/cm$^2$ thick volume of BaFCl phosphor screen has been tested as a scintillator volume sandwiched between two layers of WSFs. The phosphor screen had a transparent backing so that scintillation light could escape from both the entrance and exit surfaces of the scintillator. The light output of each WSF layer was recorded using an incident 140 kV x-ray beam, as different thicknesses of steel were introduced between the x-ray source and the detector.

FIG. 24 is a schematic illustration of an alternative x-ray detector structure 2400 that may be advantageously used in embodiment x-ray imaging apparatuses. In the illustrated structure, a light cavity 2488 takes the place of the first layer of WSFs shown in FIG. 22 and FIG. 23.

Lower-energy x-rays are preferentially absorbed in the upper regions of the scintillator volume 2274, close to the entrance surface 2276 of the scintillator. Higher energy x-rays are preferentially absorbed in the lower regions of the scintillator volume 2274, closer to the exit surface 2278. Since the scintillator volume 2274 absorbs its own scintillation light, the light from the lower-energy x-rays is preferentially emitted from the entrance surface, where it is detected by the one or more cavity photodetectors 2406 that are optically coupled to the upper light cavity 2488. Conversely, the light from the higher-energy x-rays is preferentially emitted from the exit surface 2278, where it is detected by the one or more photodetectors optically coupled to a layer of wavelength-shifting fibers (WSFs) 2482, which in turn are optically coupled to the exit surface 2278. Separate output signals from two sets of photodetectors can then be used to determine a characteristic of the energy spectrum of the incident x-rays, as illustrated and described in connection with FIG. 22.

FIGS. 25-30 are cross-sectional view diagrams of various example x-ray tube oriented relative to hoop chopper wheels as part of embodiments. Advantages or various embodiments will become further apparent via the discussion of these figures.

Figure 25:
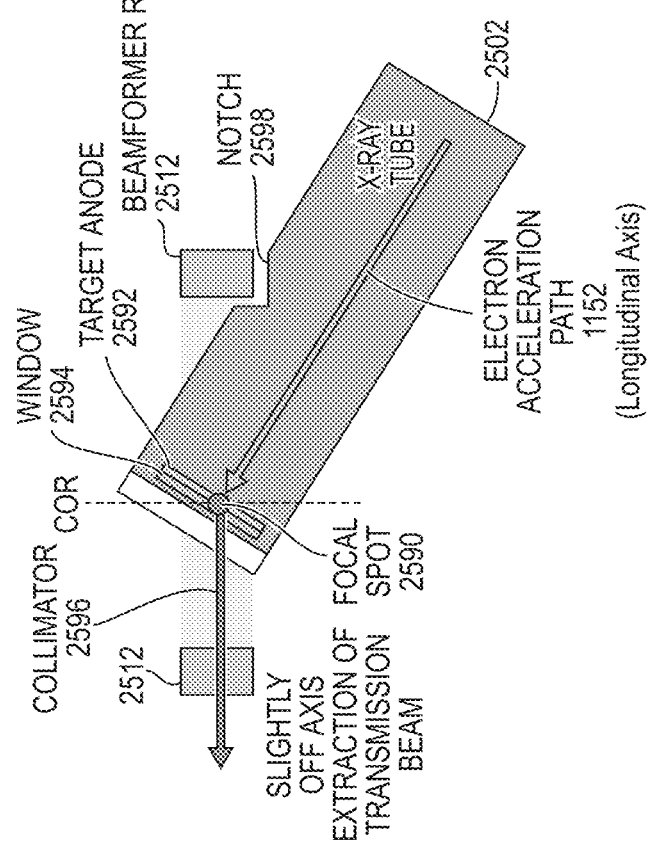

FIG. 25 shows a tilted transmission x-ray tube 2502 with in-line hoop chopper wheel 2512 (also referred to as a "beamformer ring") with a clearance notch 2598 in the tube 2502. The notch 2598 illustrates that even better, more compact form of the hoop 2512 can be achieved. Also illustrated are a collimator 2596, target anode 2592, window 2594, and focal spot 2590. The collimator 2596 can be made of a heavy metal such as tungsten, for example, and it's orientation with respect to the longitudinal axis 1152 allows for selection of the desired angle 1154 shown in FIG. 11. This configuration allows for even smaller/lighter beamforming ring. Losses from off axis transmission extraction are less than for reflection type x-ray tubes. Center of rotation (COR) is in line with the focal spot 2590, and the design maintains consistent spot side size at leading and trailing edges of a scan line of the pencil scanning beam.

Figure 26:
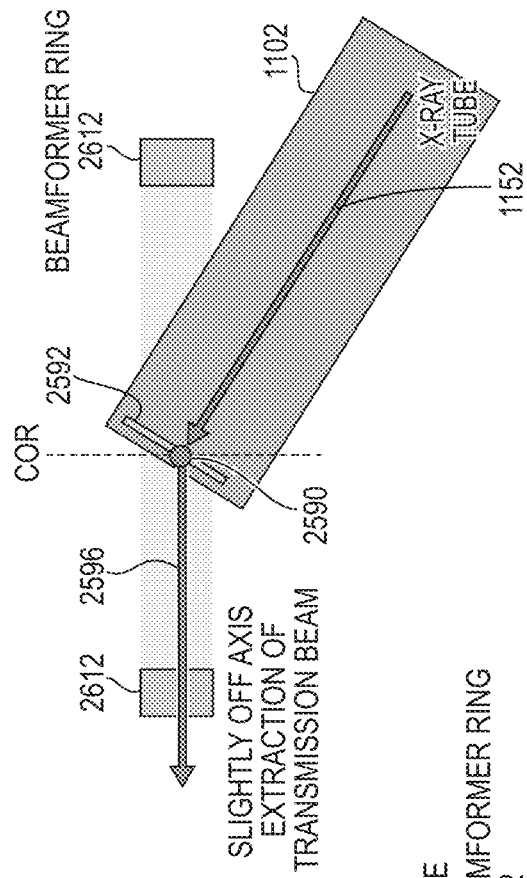

FIG. 26 is similar to FIG. 25 but illustrates design consequences of omitting the clearance notch from the x-ray tube 1102. A collimator 2796 is provided. A hoop chopper wheel 2612 is somewhat larger than for 2512 but can still be small. Tube efficiency losses from off-axis transmission extraction are less than for reflection-type x-ray tubes. COR of the hoop 2612 is in line with the focal spot 2590, and the design maintains consistent spot side size at leading/trailing edges of scan lines.

Figure 27:
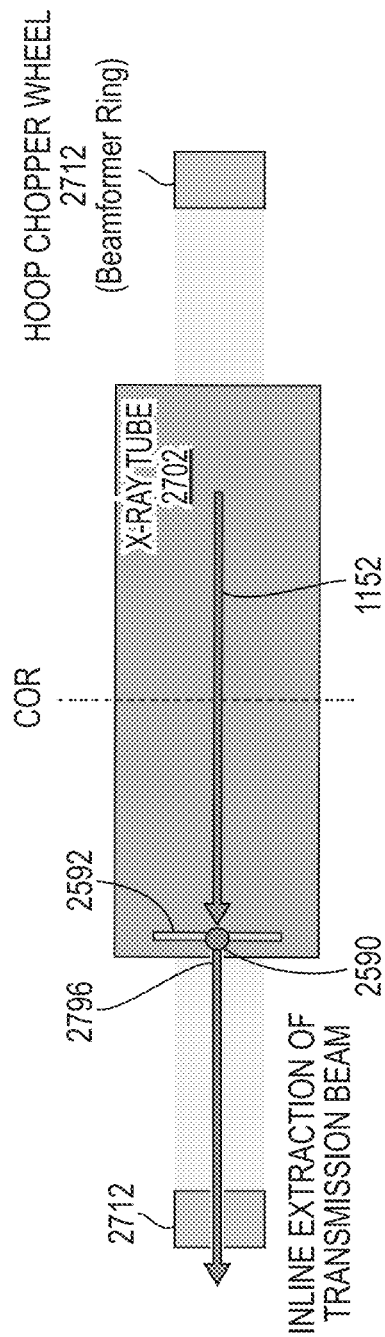

FIG. 27 shows a straight transmission x-ray tube functioning with an offset hoop chopper wheel 2712. The beamformer ring 2712 is still small. Tube efficiency losses from off-axis transmission extraction are still less than for reflection type x-ray tubes. COR of beamformer ring is in line with focal spot. It maintains consistent spot side size at leading/trailing edges of scan lines.

Figure 28:
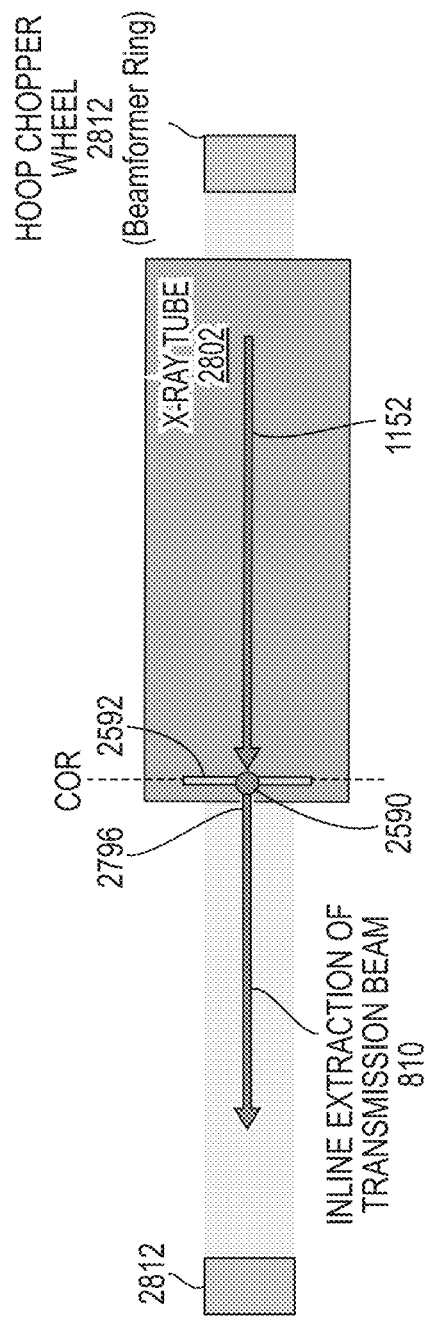

FIG. 28 shows a straight transmission x-ray tube functioning with an inline hoop chopper wheel 2812. This design has narrow interference of the beamformer in typical backscatter detection area, a larger diameter hoop 2812 to clear the tube 2802 with significant projection in front to the tube, and COR of the beamformer ring is in line with the focal spot.

FIG. 29 shows a straight transmission x-ray tube functioning with a tilted, in-line hoop chopper wheel. This design, with beamformer ring 2912, requires a smaller diameter ring, but it has to be much taller to cover beam fan angles up to 90 degrees. The projected spot is non-uniform at edges due to movement along the curvature of the ring.

FIG. 30 illustrates a reflection-type anode x-ray tube functioning with an in-line hoop chopper wheel in an embodiment. Reflection type tubes are less efficient, provide lower emissions for same power consumption, and are not ideal for battery powered systems/

Potential Claims

Various embodiments may be characterized by the potential claims listed in the paragraphs following this paragraph (and before the actual claims provided at the end of this application). These potential claims in the following clauses form a part of the written description of this application. Accordingly, subject matter of the following potential claims may be presented as actual claims in later proceedings involving this application or any application claiming priority based on this application. Inclusion of such potential claims should not be construed to mean that the actual claims do not cover the subject matter of the potential claims. Thus, a decision to not present these potential claims in later proceedings should not be construed as a donation of the subject matter to the public.

Without limitation, potential subject matter that may be claimed includes:

Clause 1. An x-ray imaging apparatus comprising:
    a holdable housing;
    an x-ray source mounted within the housing and configured to output a fan beam of x-rays; and
    a hoop chopper wheel rotatably mounted within the housing and comprising an x-ray attenuating material configured to block x-rays of the fan beam, the hoop chopper wheel defining a set of beam apertures of which each aperture is configured to pass therethrough a corresponding angular portion of x-rays from the fan beam, so that rotation of the hoop chopper wheel causes scanning of the corresponding angular portion of x-rays.

Clause 2. The apparatus of clause 1, wherein the x-ray source is a transmission-type x-ray tube configured to output the fan beam of x-rays through an exit window of the x-ray source.

Clause 3. The apparatus of clause 2, wherein the transmission-type x-ray tube is configured to output the fan beam of x-rays centered in an x-ray extraction direction forming an angle greater than 0 degrees with respect to an longitudinal axis of the transmission-type x-ray tube.

Clause 4. The apparatus of clause 3, wherein the x-ray extraction direction is defined by an orientation of a collimator.

Clause 5. The apparatus of clause 3, wherein the x-ray extraction direction forms an angle in a range of about 10 degrees to about 60 degrees with respect to the longitudinal axis.

Clause 6. The apparatus of clause 5, wherein the angle is in a range of about 20 degrees to about 50 degrees.

Clause 7. The apparatus of clause 6, wherein the angle is in a range of about 25 degrees to about 35 degrees.

Clause 8. The apparatus of clause 1, wherein a minimum distance between an outer surface of the hoop chopper wheel and a front of the housing is less than about 50 mm.

Clause 9. The apparatus of clause 8, wherein the minimum distance is less than about 30 mm.

Clause 10. The apparatus of clause 9, wherein the minimum distance is less than about 10 mm.

Clause 11. The apparatus of clause 10, wherein the minimum distance is less than about 5 mm.

Clause 12. The apparatus of clause 10, wherein the minimum distance is between about 10 mm and about 1 mm.

Clause 13. The apparatus of clause 1, further including:
- a set of x-ray detectors configured to detect incident x-rays scattered by, or transmitted through, a target object that receives x-rays of the corresponding angular portion of x-rays from the fan beam, wherein at least one x-ray detector of the set of x-ray detectors comprises:
  - a scintillator volume having an entrance surface and an exit surface, the entrance surface configured to receive the incident x-rays, the scintillator volume configured to emit scintillation light responsive to the incident x-rays, and the exit surface configured to pass a portion of the incident x-rays that traverse a thickness of the scintillator volume between the entrance surface and the exit surface;
  - at least one first photodetector configured to output a first signal responsive to scintillation light received through the entrance surface of the scintillator volume;
  - a plurality of exit surface light guides optically coupled to the exit surface of the scintillator volume; and
  - at least one second photodetector optically coupled to an end of the plurality of exit surface light guides and configured to output a second signal responsive to scintillation light received through the exit surface of the scintillator volume.

Clause 14. The apparatus of clause 13, further including a light cavity configured to direct the scintillation light received through the entrance surface to the at least one first photodetector.

Clause 15. The apparatus of clause 13, further comprising a plurality of entrance surface light guides optically coupled to the entrance surface of the scintillator volume, wherein the at least one first photodetector is optically coupled to an end of the first plurality of light guides;

Clause 16. The apparatus of clause 13, further comprising a spectrum analyzer configured to receive the first and second signals and to determine a characteristic of an energy spectrum of the incident x-rays based on the first and second signals.

Clause 17. The apparatus of clause 13, further comprising an image generator configured to generate an image based on the detected x-rays.

Clause 18. The apparatus of clause 1, wherein a focal spot of the x-ray source is substantially centered on a rotational axis of the hoop chopper wheel.

Clause 19. The apparatus of clause 1, wherein a focal spot of the x-ray source has a substantial forward radial offset from a rotational axis of the hoop chopper wheel, the substantial forward radial offset configured to decrease a distance from the focal spot to a beam aperture of the set of apertures that is irradiated.

Clause 20. The apparatus of clause 1, wherein a focal spot of the x-ray source has a substantial reverse radial offset from a rotational axis of the hoop chopper wheel, the substantial reverse radial offset configured to increase a distance from the focal spot to a beam aperture of the set of apertures that is irradiated.

Clause 21. The apparatus of clause 1, wherein the set of beam apertures are of a shape selected from the group consisting of circular, square, ellipsoidal, trapezoidal, rectangular, and combinations thereof.

Clause 22. The apparatus of clause 1, wherein the set of beam apertures includes at least two beam apertures configured to pass therethrough two distinct angular portions of x-rays from the fan beam.

Clause 23. The apparatus of clause 1, wherein the hoop chopper wheel is made of a material selected from the group consisting of tungsten, lead, another highly attenuating material, a composite, and combinations thereof.

Clause 24. The apparatus of clause 1, wherein the hoop chopper wheel comprises two or more sub-hoops.

Clause 25. The apparatus of clause 1, wherein the hoop chopper wheel comprises a plurality of hoop segments configured to be joined together.

Clause 26. The apparatus of clause 1, further including a support mechanism by which the hoop chopper wheel is rotatably mounted, the support mechanism including a shaft that extends through a set of bearings, and wherein the support mechanism is selected from the group consisting of a cup mechanism, a plate mechanism, and combinations thereof.

Clause 27. The apparatus of clause 26, wherein the set of bearings is mounted directly to the x-ray source.

Clause 28. The apparatus of clause 1, further including a support mechanism by which the hoop chopper wheel is rotatably mounted, the support mechanism including a roller assembly, and wherein the support mechanism is selected from the group consisting of a cup mechanism, a plate mechanism, and combinations thereof.

Clause 29. The apparatus of any of clauses 26-28, wherein the support mechanism comprises a material selected from the group consisting of aluminum, steel, carbon fiber, composite, and combinations thereof.

Clause 30. The apparatus of clause 1, further including a hoop-type bearing to which the hoop chopper wheel is rotatably mounted.

Clause 31. The apparatus of clause 1, wherein the set of beam apertures includes a plurality of subsets of apertures, the apparatus further including a selection mechanism configured to enable a selectable subset of apertures of the plurality of subsets of apertures to be irradiated by the fan beam of x-rays during rotation of the hoop chopper wheel.

Clause 32. The apparatus of clause 31, wherein different subsets of apertures of the plurality of subsets of apertures have different respective dimensions.

Clause 33. The apparatus of clause 31, wherein the selection mechanism is a translation mechanism configured to translate the hoop chopper wheel in a direction substantially normal to a plane of the fan beam in order to enable selection of the subset of apertures.

Clause 34. The apparatus of clause 1, further including a translation mechanism configured to enable the hoop chopper wheel to be moved out of the fan beam selectively so as not to block x-rays of the fan beam, thereby allowing the fan beam to exit a front of the apparatus.

Clause 35. The apparatus of clause 1, further including a shutter configured to be moved to prevent, selectively, the scanning, angular portion of the x-rays from exiting the apparatus.

Clause 36. The apparatus of clause 35, wherein the shutter is configured to be rotated in a plane of rotation of the hoop chopper wheel Clause 37. The apparatus of clause 35, wherein the shutter is configured to be translated in a plane perpendicular to a plane of rotation of the hoop chopper wheel.

Clause 38. The apparatus of clause 1, wherein apertures of the set of apertures have chamfered edges.

Clause 39. The apparatus of clause 1, wherein at least one beam aperture of the set of beam apertures is a slot.

Clause 40. The apparatus of clause 1, wherein the hoop chopper wheel includes an integrated drive feature selected from the group consisting of a gear, a chain sprocket, a drive belt pathway, and combinations thereof.

Clause 41. The apparatus of clause 1 that incorporates facets or drilled holes to balance a hoop with asymmetric apertures.

Clause 42. The apparatus of clause 1, further including a laser configured to emit visible light through the set of beam apertures.

Clause 43. The apparatus of clause 1, further including a pre-collimator configured to block scattered x-rays of the fan beam between the x-ray source and an interior surface of the hoop chopper wheel.

Clause 44. The apparatus of clause 1, wherein the hoop includes an overlap feature configured to overlap a pre-collimator to prevent scatter escape from a source side of the hoop.

Clause 45. An x-ray imaging apparatus comprising:
a housing;
a transmission-type x-ray tube mounted within the housing and configured to output a fan beam of x-rays, through an exit window of the transmission-type x-ray tube, centered in an x-ray extraction direction forming an angle greater than 0 degrees with respect to an longitudinal axis of the transmission-type x-ray tube; and
a hoop chopper wheel rotatably mounted within the housing and comprising an x-ray attenuating material configured to block x-rays of the fan beam, the hoop chopper wheel defining a set of beam apertures of which each aperture is configured to pass therethrough a corresponding angular portion of x-rays from the fan beam, so that rotation of the hoop chopper wheel causes scanning of the corresponding angular portion of x-rays.

Clause 46. The apparatus of clause 45, wherein the x-ray extraction direction forms an angle in a range of about 10 degrees to about 60 degrees with respect to the longitudinal axis.

Clause 47. The apparatus of clause 46, wherein the angle is in a range of about 20 degrees to about 50 degrees.

Clause 48. The apparatus of clause 47, wherein the angle is in a range of about 25 degrees to about 35 degrees.

Clause 49. The apparatus of clause 45, wherein a minimum distance between an outer surface of the hoop chopper wheel and a front of the housing is less than about 50 mm.

Clause 50. The apparatus of clause 49, wherein the minimum distance is less than about 30 mm.

Clause 51. The apparatus of clause 50, wherein the minimum distance is less than about 10 mm from a front of the housing.

Clause 52. The apparatus of clause 51, wherein the minimum distance is less than about 5 mm from a front of the housing.

Clause 53. The apparatus of clause 52, wherein the minimum distance is between about 10 mm and about 1 mm.

Clause 54. The apparatus of clause 45, further including any of the features of any of clauses 13-44.

Clause 55. An x-ray tube comprising:
a transmission anode configured to receive electrons accelerated in a longitudinal axis of the x-ray tube and to produce source x-rays thereby;
an x-ray collimator configured to collimate the source x-rays for output as a fan beam of x-rays centered in an x-ray extraction direction forming an angle greater than 0 degrees with respect to the longitudinal axis of the transmission-type x-ray tube.

Clause 56. The x-ray tube of clause 55, wherein the x-ray extraction direction is defined by an orientation of a collimator.

Clause 57. The x-ray tube of clause 55, wherein the angle is in a range of 15 degrees to 45 degrees.

Clause 58. The x-ray tube of clause 57, wherein the angle is in a range of 20 degrees to 40 degrees.

Clause 59. The x-ray tube of clause 58, wherein the angle is in a range of 25 degrees to 35 degrees.

Clause 60. An x-ray detector comprising:
a scintillator volume having an entrance surface and an exit surface, the entrance surface configured to receive incident x-rays, the scintillator volume configured to emit scintillation light responsive to the incident x-rays, and the exit surface configured to pass a portion of the incident x-rays that traverse a thickness of the scintillator volume between the entrance surface and the exit surface;
at least one first photodetector configured to output a first signal responsive to scintillation light received through the entrance surface of the scintillator volume;
a plurality of exit surface light guides optically coupled to the exit surface of the scintillator volume; and
at least one second photodetector optically coupled to an end of the plurality of exit surface light guides and configured to output a second signal responsive to scintillation light received through the exit surface of the scintillator volume.

Clause 61. The x-ray detector of clause 60, further comprising a light cavity situated adjacent to the entrance surface of the scintillation volume, the light cavity configured to direct the scintillation light received through the entrance surface to the at least one first photodetector.

Final Considerations

The embodiments of the invention described above are intended to be merely exemplary; numerous variations and modifications will be apparent to those skilled in the art. All such variations and modifications are intended to be within the scope of the present invention as defined in any appended claims.

While example embodiments have been particularly shown and described, it will be understood by those skilled in the art that various changes in form and details may be made therein without departing from the scope of the embodiments encompassed by the appended claims.

The teachings of all patents, published applications and references cited herein are incorporated by reference in their entirety.

What is claimed is:

1. An x-ray imaging apparatus comprising:
    a holdable housing;
    an x-ray source mounted within the housing and configured to output a fan beam of x-rays, wherein the x-ray source is a transmission-type x-ray tube configured to output the fan beam of x-rays through an exit window of the x-ray source and centered in an x-ray extraction direction forming an angle greater than 0 degrees with respect to a longitudinal axis of the transmission-type x-ray tube; and
    a hoop chopper wheel rotatably mounted within the housing and comprising an x-ray attenuating material configured to block x-rays of the fan beam, the hoop chopper wheel defining a set of beam apertures of which each aperture is configured to pass therethrough a corresponding angular portion of x-rays from the fan beam, so that rotation of the hoop chopper wheel causes scanning of the corresponding angular portion of x-rays.

2. The apparatus of claim 1, wherein the x-ray extraction direction is defined by an orientation of a collimator.

3. The apparatus of claim 1, wherein the x-ray extraction direction forms an angle in a range of about 10 degrees to about 60 degrees with respect to the longitudinal axis.

4. The apparatus of claim 3, wherein the angle is in a range of about 20 degrees to about 50 degrees.

5. The apparatus of claim 4, wherein the angle is in a range of about 25 degrees to about 35 degrees.

6. The apparatus of claim 1, wherein a minimum distance between an outer surface of the hoop chopper wheel and a front of the housing is less than about 50 mm.

7. The apparatus of claim 6, wherein the minimum distance is less than about 30 mm.

8. The apparatus of claim 7, wherein the minimum distance is less than about 10 mm.

9. The apparatus of claim 8, wherein the minimum distance is less than about 5 mm.

10. The apparatus of claim 8, wherein the minimum distance is between about 10 mm and about 1 mm.

11. The apparatus of claim 1, further including a set of x-ray detectors configured to detect incident x-rays scattered by, or transmitted through, a target object that receives x-rays of the corresponding angular portion of x-rays from the fan beam, wherein at least one x-ray detector of the set of x-ray detectors comprises:
    a scintillator volume having an entrance surface and an exit surface, the entrance surface configured to receive the incident x-rays, the scintillator volume configured to emit scintillation light responsive to the incident x-rays, and the exit surface configured to pass a portion of the incident x-rays that traverse a thickness of the scintillator volume between the entrance surface and the exit surface;
    at least one first photodetector configured to output a first signal responsive to scintillation light received through the entrance surface of the scintillator volume;
    a plurality of exit surface light guides optically coupled to the exit surface of the scintillator volume; and
    at least one second photodetector optically coupled to an end of the plurality of exit surface light guides and configured to output a second signal responsive to scintillation light received through the exit surface of the scintillator volume.

12. The apparatus of claim 11, further including a light cavity configured to direct the scintillation light received through the entrance surface to the at least one first photodetector.

13. The apparatus of claim 11, further comprising a plurality of entrance surface light guides optically coupled to the entrance surface of the scintillator volume, wherein the at least one first photodetector is optically coupled to an end of the first plurality of light guides.

14. The apparatus of claim 11, further comprising a spectrum analyzer configured to receive the first and second signals and to determine a characteristic of an energy spectrum of the incident x-rays based on the first and second signals.

15. The apparatus of claim 11, further comprising an image generator configured to generate an image based on the detected x-rays.

16. The apparatus of claim 1, wherein a focal spot of the x-ray source is substantially centered on a rotational axis of the hoop chopper wheel.

17. The apparatus of claim 1, wherein a focal spot of the x-ray source has a substantial forward radial offset from a rotational axis of the hoop chopper wheel, the substantial forward radial offset configured to decrease a distance from the focal spot to a beam aperture of the set of apertures that is irradiated.

18. The apparatus of claim 1, wherein a focal spot of the x-ray source has a substantial reverse radial offset from a rotational axis of the hoop chopper wheel, the substantial reverse radial offset configured to increase a distance from the focal spot to a beam aperture of the set of apertures that is irradiated.

19. An x-ray imaging apparatus comprising:
    a housing;
    a transmission-type x-ray tube mounted within the housing and configured to output a fan beam of x-rays, through an exit window of the transmission-type x-ray tube, centered in an x-ray extraction direction forming an angle greater than 0 degrees with respect to an longitudinal axis of the transmission-type x-ray tube; and
    a hoop chopper wheel rotatably mounted within the housing and comprising an x-ray attenuating material configured to block x-rays of the fan beam, the hoop chopper wheel defining a set of beam apertures of which each aperture is configured to pass therethrough a corresponding angular portion of x-rays from the fan beam, so that rotation of the hoop chopper wheel causes scanning of the corresponding angular portion of x-rays.

20. The apparatus of claim 19, wherein the x-ray extraction direction forms an angle in a range of about 10 degrees to about 60 degrees with respect to the longitudinal axis.

21. The apparatus of claim 20, wherein the angle is in a range of about 20 degrees to about 50 degrees.

22. The apparatus of claim 21, wherein the angle is in a range of about 25 degrees to about 35 degrees.

23. The apparatus of claim 19, wherein a minimum distance between an outer surface of the hoop chopper wheel and a front of the housing is less than about 50 mm.

24. The apparatus of claim 23, wherein the minimum distance is less than about 30 mm.

25. The apparatus of claim 24, wherein the minimum distance is less than about 10 mm from a front of the housing.

26. The apparatus of claim 25, wherein the minimum distance is less than about 5 mm from a front of the housing.

27. The apparatus of claim 26, wherein the minimum distance is between about 10 mm and about 1 mm.

\* \* \* \* \*